United States Patent
Baker et al.

(10) Patent No.: US 8,575,214 B2
(45) Date of Patent: Nov. 5, 2013

(54) MGLU 2/3 AGONISTS

(71) Applicant: Eli Lilly and Company, Indianapolis, IN (US)

(72) Inventors: Stephen Richard Baker, Isle of Man (GB); Christopher David Beadle, Bierton (GB); Barry Peter Clark, Lower Froyle (GB); James Allen Monn, Indianapolis, IN (US); Lourdes Prieto, Madrid (ES)

(73) Assignee: Eli Lilly and Company, Indianapolis, MN (US)

( * ) Notice: Subject to any disclaimer, the term of this patent is extended or adjusted under 35 U.S.C. 154(b) by 0 days.

(21) Appl. No.: 13/752,432

(22) Filed: Jan. 29, 2013

(65) Prior Publication Data

US 2013/0197079 A1    Aug. 1, 2013

Related U.S. Application Data

(60) Provisional application No. 61/619,139, filed on Apr. 2, 2012.

(30) Foreign Application Priority Data

Feb. 1, 2012 (EP) .................... 12382038

(51) Int. Cl.
  *A61K 31/235* (2006.01)
  *A61K 31/44* (2006.01)
(52) U.S. Cl.
  USPC .......................... 514/532; 514/534
(58) Field of Classification Search
  USPC ................. 514/532, 534
  See application file for complete search history.

(56) References Cited

FOREIGN PATENT DOCUMENTS

| WO | 97/17952 A1 | 5/1997 |
|---|---|---|
| WO | 9718199 A1 | 5/1997 |
| WO | 98/51655 A1 | 11/1998 |
| WO | 02/055481 A1 | 7/2002 |
| WO | 02/055485 A1 | 7/2002 |
| WO | 03/104217 A2 | 12/2003 |
| WO | 2011/084437 A1 | 7/2011 |

OTHER PUBLICATIONS

M.J. O'Neill et al., Recent Developments in Metabotropic Glutamate Receptors as Novel Drug Targets, Drugs of the Future, 2010, 35(4), 307-324.

Patil, S., et al., "Activation of mGlu2/3 receptors as a new approach to treat schizophrenia: a randomized Phase 2 clinical trial," Nature Medicine, 13(9):1102-1107 and supplementary tables and figures (2007).

*Primary Examiner* — San-Ming Hui
(74) *Attorney, Agent, or Firm* — R. Craig Tucker; Danica Hostettler

(57) ABSTRACT

The present invention provides novel mGlu2/3 agonists of the formula

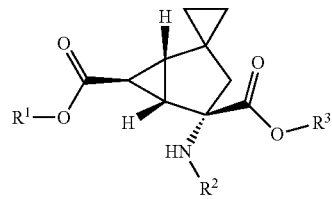

wherein $R^1$, $R^2$, and $R^3$ are as defined herein, for use in the treatment of neurological or psychiatric disorders.

35 Claims, No Drawings

MGLU 2/3 AGONISTS

The present invention relates to mGlu2/3 agonists, more specifically, to a novel 4-substituted bicyclo[3.1.0]hexane and prodrugs thereof, pharmaceutical compositions thereof, and therapeutic uses thereof.

L-Glutamate is the major excitatory neurotransmitter in the central nervous system and is referred to as an excitatory amino acid. The metabotropic glutamate (mGlu) receptors are G-protein-coupled receptors that modulate neuronal excitability. Treatment of neurological or psychiatric disorders has been linked to selective activation of mGlu excitatory amino acid receptors. More particularly, studies demonstrate that mGlu2/3 agonists have analgesic, antipsychotic, anxiolytic, antidepressant, and neuroprotective properties. Therefore, these properties of mGlu2/3 agonists may be useful in the treatment of neurological disorders, such as chronic pain conditions, or psychiatric disorders, such as schizophrenia, bipolar disorder, also known as manic depressive disorder, generalized anxiety disorder, and post traumatic stress disorder.

WO9717952 discloses certain 4-substituted bicyclo[3.1.0] hexane compounds asserted to be excitatory amino acid receptor antagonists.

Excessive glutamatergic tone has been implicated in many disease states of the central nervous system; however, effective agents to correct such pathophysiological states are lacking in clinical practice. In particular, clinical application has not been realized due to a lack of mGlu2/3 agonists with appropriate drug-like properties. Thus, there still exists a need for potent, efficacious mGlu2/3 agonists. The present invention provides a novel 4-substituted bicyclo[3.1.0]hexane, and prodrugs thereof, that are potent and effective mGlu2/3 agonists. Particular prodrugs within the scope of the present invention are well absorbed after oral administration and subsequently hydrolyzed to release the active metabolite into the systemic circulation and, therefore, are suitable for clinical development. Such new compounds of the present invention could address the need for potent, effective treatments of neurological disorders, such as chronic pain conditions including persistent pain, neuropathic pain, chronic inflammatory pain, or visceral pain, or psychiatric disorders, such as schizophrenia, bipolar disorder, generalized anxiety disorder, or post traumatic stress disorder.

The present invention provides a compound of Formula I

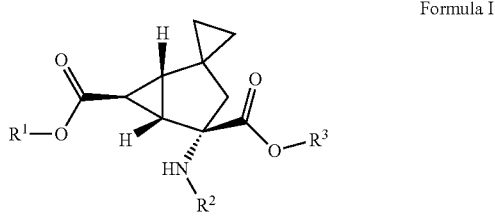

Formula I wherein
$R^1$ is hydrogen, $R^2$ is hydrogen, and $R^3$ is hydrogen;
$R^1$ is hydrogen, $R^2$ is (2S)-2-aminopropanoyl, and $R^3$ is hydrogen;
$R^1$ is hydrogen, $R^2$ is (2S)-2-amino-4-methylsulfanyl-butanoyl, and $R^3$ is hydrogen;
$R^1$ is hydrogen, $R^2$ is 2-aminoacetyl, and $R^3$ is hydrogen;
$R^1$ is benzyl, $R^2$ is hydrogen, and $R^3$ is benzyl; or
$R^1$ is (2-fluorophenyl)methyl, $R^2$ is hydrogen, and $R^3$ is (2-fluorophenyl)methyl;
or a pharmaceutically acceptable salt thereof.

The present invention provides (1S,2S,5R,6S)-2-aminospiro[bicyclo[3.1.0]hexane-4,1'-cyclopropane]-2,6-dicarboxylic acid, or a pharmaceutically acceptable salt thereof.

As a particular embodiment, the present invention provides (1S,2S,5R,6S)-2-aminospiro[bicyclo[3.1.0]hexane-4,1'-cyclopropane]-2,6-dicarboxylic acid.

As a particular embodiment, the present invention provides the hydrochloric acid salt of (1S,2S,5R,6S)-2-aminospiro[bicyclo[3.1.0]hexane-4,1'-cyclopropane]-2,6-dicarboxylic acid.

The present invention provides (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof.

As a particular embodiment, the present invention provides (1S,2S,5R,6S)-2-[[(2S)-2-aminopropanoyl]amino]spiro[bicyclo[3.1.0]hexane-4,1'-cyclopropane]-2,6-dicarboxylic acid hydrochloride.

As a particular embodiment, the present invention provides (1S,2S,5R,6S)-2-[[(2S)-2-aminopropanoyl]amino]spiro[bicyclo[3.1.0]hexane-4,1'-cyclopropane]-2,6-dicarboxylic acid; 1,4-dioxane (1:0.5); hydrochloride.

The present invention provides (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof.

As a particular embodiment, the present invention provides (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid hydrochloride.

The present invention provides (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof.

As a particular embodiment, the present invention provides (1S,2S,5R,6S)-2-[(2-aminoacetyl)amino]spiro[bicyclo[3.1.0]hexane-4,1'-cyclopropane]-2,6-dicarboxylic acid hydrochloride.

The present invention provides dibenzyl (1S,2S,5R,6S)-2-aminospiro[bicyclo[3.1.0]hexane-4,1'-cyclopropane]-2,6-dicarboxylate, or a pharmaceutically acceptable salt thereof.

As a particular embodiment, the present invention provides dibenzyl (1S,2S,5R,6S)-2-aminospiro[bicyclo[3.1.0]hexane-4,1'-cyclopropane]-2,6-dicarboxylate; 1,4-dioxane; hydrochloride.

The present invention provides bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof.

As a particular embodiment, the present invention provides bis[(2-fluorophenyl)methyl](1S,2S,5R,6S)-2-aminospiro[bicyclo[3.1.0]hexane-4,1'-cyclopropane]-2,6-dicarboxylate hydrochloride.

The present invention provides a pharmaceutical composition comprising (1S,2S,5R,6S)-2-aminospiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof, dibenzyl (1S,2S,5R,6S)-2-aminospiro[bicyclo[3.1.0]hexane-4,1'-cyclopropane]-2,6-dicarboxylate, or a pharmaceutically acceptable salt thereof, or bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof, together with a pharmaceutically acceptable carrier and optionally other therapeutic ingredients.

The present invention provides a pharmaceutical composition comprising (1S,2S,5R,6S)-2-aminospiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof, dibenzyl (1S,2S,5R,6S)-2-aminospiro[bicyclo[3.1.0]hexane-4,1'-cyclopropane]-2,6-dicarboxylate, or a pharmaceutically acceptable salt thereof, or bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof, and a pharmaceutically acceptable carrier, diluent, or excipient.

The present invention provides a method of treating a neurological or psychiatric disorder, comprising administering to a patient in need thereof an effective amount of (1S,2S,5R,6S)-2-aminospiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof, dibenzyl (1S,2S,5R,6S)-2-aminospiro[bicyclo[3.1.0]hexane-4,1'-cyclopropane]-2,6-dicarboxylate, or a pharmaceutically acceptable salt thereof, or bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof.

The present invention provides the use of (1S,2S,5R,6S)-2-aminospiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof, (1S,2 S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof, dibenzyl (1S,2S,5R,6S)-2-aminospiro[bicyclo[3.1.0]hexane-4,1'-cyclopropane]-2,6-dicarboxylate, or a pharmaceutically acceptable salt thereof, or bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof, for the manufacture of a medicament for the treatment of a neurological or psychiatric disorder.

The present invention provides (1S,2S,5R,6S)-2-aminospiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof, dibenzyl (1S,2S,5R,6S)-2-aminospiro[bicyclo[3.1.0]hexane-4,1'-cyclopropane]-2,6-dicarboxylate, or a pharmaceutically acceptable salt thereof, or bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof, for use in therapy. The present invention also provides (1S,2S,5R,6S)-2-aminospiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof, (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof, dibenzyl (1S,2S,5R,6S)-2-aminospiro[bicyclo[3.1.0]hexane-4,1'-cyclopropane]-2,6-dicarboxylate, or a pharmaceutically acceptable salt thereof, or bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof, for use in the treatment of a neurological or psychiatric disorder.

Furthermore, the present invention provides preferred embodiments of the methods and uses as described herein, in which the neurological disorder is selected from the group consisting of persistent pain, neuropathic pain, chronic inflammatory pain, and visceral pain, and the psychiatric disorder is selected from the group consisting of schizophrenia, bipolar disorder, generalized anxiety disorder, and post traumatic stress disorder.

As used above, and throughout the description of the invention, the following terms, unless otherwise indicated, shall be understood to have the following meanings:

"Compound(s) of the invention" and "compound(s) of the present invention" include prodrugs, active compounds, and/or active metabolites. A "prodrug" is a class of drugs, initially in inactive form that is converted into active form in the body by normal metabolic processes, wherein at least one of $R^1$, $R^2$, and $R^3$ in Formula I is other than hydrogen (e.g. $R^1$ is hydrogen, $R^2$ is (2S)-2-aminopropanoyl, and $R^3$ is hydrogen; $R^1$ is hydrogen, $R^2$ is (2S)-2-amino-4-methylsulfanyl-butanoyl, and $R^3$ is hydrogen; $R^1$ is hydrogen, $R^2$ is 2-aminoacetyl, and $R^3$ is hydrogen; $R^1$ is benzyl, $R^2$ is hydrogen, and $R^3$ is benzyl; or $R^1$ is (2-fluorophenyl)methyl, $R^2$ is hydrogen, and $R^3$ is (2-fluorophenyl)methyl). An "active compound" or "active" is another name for an active form administered to the body, for example, intravenously or intraperitoneally, wherein $R^1$, $R^2$, and $R^3$ in Formula I are hydrogen. An "active metabolite" is another name for an active form resulting from such a conversion of a prodrug in the body by normal metabolic processes, wherein $R^1$, $R^2$, and $R^3$ in Formula I are hydrogen.

A "pharmaceutically acceptable carrier, diluent, or excipient" is a medium generally accepted in the art for the delivery of biologically active agents to mammals, e.g., humans.

"Pharmaceutically acceptable salts" refers to the relatively non-toxic, inorganic and organic salts of compounds of the present invention.

"Therapeutically effective amount" or "effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

Under standard nomenclature used throughout this disclosure, the terminal portion of the designated side chain is described first, followed by the adjacent functionality toward the point of attachment. For example, a methylsulfonyl substituent is equivalent to $CH_3$—$SO_2$—.

The compounds of the present invention are capable of reaction, for example, with a number of inorganic and organic acids to form pharmaceutically acceptable acid addition salts or basic addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

The compounds of the present invention are preferably formulated as pharmaceutical compositions using a pharmaceutically acceptable carrier, diluent, or excipient and administered by a variety of routes. Preferably, such compositions are for oral or intravenous administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The compound of the present invention actually administered will be determined by a physician under the relevant circumstances, including the condition to be treated, the chosen route of administration, the actual compound or compounds of the present invention administered, the age, weight, and response of the individual patient, and the severity of the patient's symptoms. Dosages per day normally fall within the range of about 0.1 to about 300 mg. In some instances dosage levels below the lower limit of the aforesaid range may be more than adequate, while in other cases still larger doses may be employed.

The compounds of the present invention, or pharmaceutically acceptable salts thereof, may be prepared by a variety of procedures known in the art, as well as those described in the Preparations and Examples below. The specific synthetic steps for each of the routes described may be combined in different ways to prepare the compounds of the invention, or pharmaceutically acceptable salts thereof.

The substituents, unless otherwise indicated, are as previously defined. The reagents and starting materials are generally readily available to one of ordinary skill in the art. Others may be made by standard techniques of organic and heterocyclic chemistry, techniques which are analogous to the syntheses of known structurally similar active compounds and prodrugs, and the procedures described in the Preparations and Examples which follow including any novel procedures. The naming of the following Preparations and Examples is done using Symyx Draw 3.1.

As used herein, the following terms have the meanings indicated: "HPLC" refers to high-pressure liquid chromatography; "LC" refers to liquid chromatography; "MS (ES+)" refers to mass spectroscopy using electrospray ionization; "MS" refers to mass spectroscopy; "SFC" refers to supercritical fluid chromatography; "NMR" refers to nuclear magnetic resonance; "TLC" refers to thin layer chromatography; "RT" refers to retention time; "UV" refers to ultraviolet; "EDTA" refers to ethylenediaminetetraacetic acid; "PBS" refers to phosphate buffered saline; "PCR" refers to polymerase chain reaction; "SCX" refers to strong cation exchange; and "HLB" refers to Hydrophilic-Lipophilic Balance.

Preparation 1

Ditert-butyl (1S,2S,5R,6S)-2-(tert-butoxycarbonylamino)-4-methylene-bicyclo[3.1.0]hexane-2,6-dicarboxylate

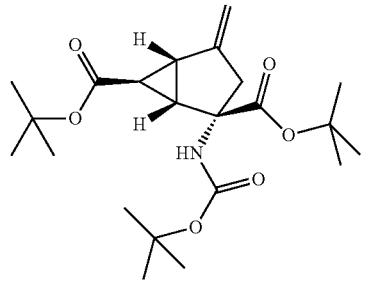 [SMILES: C=C1C[C@@](NC(=O)OC(C)(C)C)(C(=O)OC(C)(C)C)[C@H]2[C@@H]1[C@@H]2C(=O)OC(C)(C)C]

Charge an oven-dried 250 mL round-bottom flask with methyltriphenylphosphonium bromide (5.41 g, 14.9 mmol) and tetrahydrofuran (93 mL). Cool the suspension to 0° C. and add dropwise 1M solution of sodium bis(trimethylsilyl)amide in tetrahydrofuran (16.08 mL, 16.08 mmol). Stir the resultant bright yellow mixture at 0° C. for 20 minutes before adding a solution of ditert-butyl (1S,2S,5R,6R)-2-(tert-butoxycarbonylamino)-4-oxo-bicyclo[3.1.0]hexane-2,6-dicarboxylate (5.09 g, 12.4 mmol, see WO03/104217/A2 for synthesis details) in tetrahydrofuran (31 mL). Allow the reaction to warm to room temperature and stir for 16 hours. Partition the mixture between ethyl acetate (500 mL) and water (350 mL). Discard the aqueous and wash the organic phase with brine (200 mL). Dry the organic phase over magnesium sulfate, filter and concentrate under reduced pressure. Purify by flash chromatography eluting with ethyl acetate:iso-hexane (5:95 to 20:80) to yield the title compound as a white solid (4.84 g, 11.2 mmol). $^1$H NMR (CDCl$_3$) δ 1.45 (m, 27H), 1.87 (t, J=2.9 Hz, 1H), 1.98 (m, 1H), 2.43 (m, 2H), 3.07 (br m, 1H), 4.86 (br s, 1H), 5.03 (d, J=2 Hz, 1H), 5.1-5.3 (br s, 1H).

Preparation 2

Ditert-butyl (1S,2S,5R,6S)-2-(tert-butoxycarbonylamino)spiro[bicyclo[3.1.0]hexane-4,1'-cyclopropane]-2,6-dicarboxylate

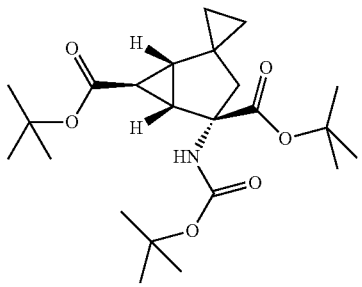 [SMILES: CC(C)(C)OC(=O)N[C@@]1(C(=O)OC(C)(C)C)CC2(CC2)[C@H]2[C@H](C(=O)OC(C)(C)C)[C@H]21]

Prepare an ethanol free solution of diazomethane in diethyl ether by charging the cold-finger of an Aldrich mini-Diazald apparatus with cardice and iso-propanol filling it one third. In the reaction portion of the apparatus place a solution of potassium hydroxide (740 mg, 13.2 mmol) in water (1.5 mL). To this solution add a mixture of diethylene glycol monoethyl ether (4 mL) and diethyl ether (2.4 mL). Dissolve N-methyl-N'-nitro-N-nitrosoguanidine (1 g, 6.8 mmol) in a mixture of diethyl ether (13 mL) and diethylene glycol monoethyl ether (4 mL). Place this solution in a dropping funnel with smooth glass joints and fit to the mini-Diazald apparatus. Warm the potassium hydroxide solution in a water bath held at 70° C., ensuring that the collection flask and a bubbler filled with diethyl ether at the outlet of the apparatus are both cooled in a cardice/iso-propanol bath. Allow the solution of N-methyl-N'-nitro-N-nitrosoguanidine to add at a rate equal to that of the resultant distillation. Once distillation is complete, add additional diethyl ether dropwise through the dropping funnel until condensate on the cold finger becomes colorless. Store the resultant solution in a cardice/iso-propanol bath until needed. Suspend palladium acetate (17.2 mg; 76.5 µmol) in diethyl ether (10 mL). Decant and filter the resulting pale brown solution and add carefully to a mixture of the diazomethane solution ditert-butyl (1S,2S,5R,6S)-2-(tert-butoxycarbonylamino)-4-methylene-bicyclo[3.1.0]hexane-2,6-dicarboxylate (330 mg, 765.5 µmol) and diethyl ether (10 mL) which has been allowed to reach ambient temperature. Once gas evolution has ceased, filter the resulting suspension and concentrate under reduced pressure to yield 260 mg of a mixture of unreacted ditert-butyl (1S,2S,5R,6S)-2-(tert-butoxycarbonylamino)-4-methylene-bicyclo[3.1.0]hexane-2,6-dicarboxylate and title compound.

Prepare an ethanol free solution of diazomethane in diethyl ether from a solution of potassium hydroxide (2.5 g, 44.6 mmol) in water (4 mL), diethylene glycol monoethyl ether (14 mL) and diethyl ether (8 mL) and N-methyl-N'-nitro-N-nitrosoguanidine (4 g, 27.2 mmol) in a mixture of diethyl ether (30 mL) and diethylene glycol monoethyl ether (15 mL). Take the resulting solution of diazomethane and add it portion wise over 30 minutes to a suspension of palladium acetate (20 mg, 89.1 µmol) in a solution of the previously prepared mixture of unreacted ditert-butyl (1S,2S,5R,6S)-2-(tert-butoxycarbonylamino)-4-methylene-bicyclo[3.1.0]hexane-2,6-dicarboxylate and title compound (260 mg) in diethyl ether (3 mL). Once gas evolution has ceased, leave to stand overnight, then filter through a phase separator frit and concentrate under reduced pressure to yield a dark oil. Purify by flash chromatography eluting with ethyl acetate:iso-hexane (0:100 to 75:25) to yield 185 mg of a mixture of unreacted ditert-butyl (1S,2S,5R,6S)-2-(tert-butoxycarbonylamino)-4-methylene-bicyclo[3.1.0]hexane-2,6-dicarboxylate and title compound.

Prepare an ethanol free solution of diazomethane in diethyl ether from a solution of potassium hydroxide (3.2 g, 57 mmol) in water (5 mL), diethylene glycol monoethyl ether (4 mL) and diethyl ether (10 mL) and N-methyl-N'-nitro-N-nitrosoguanidine (5 g, 34 mmoles) in a mixture of diethyl ether (35 mL) and diethylene glycol monoethyl ether (15 mL). Take the resulting solution of diazomethane and add it portionwise over 60 minutes to a suspension of palladium acetate (20 mg, 89.1 µmol) in a solution of the previously prepared mixture of unreacted ditert-butyl (1S,2S,5R,6S)-2-(tert-butoxycarbonylamino)-4-methylene-bicyclo[3.1.0]hexane-2,6-dicarboxylate and title compound (185 mg) in diethyl ether (2 mL). Once gas evolution has ceased, leave to stand for 30 minutes, filter and concentrate under reduced pressure to yield a yellow oil. Purify by mass guided HPLC (RT=6.4 minutes (UV), 6.37 minutes (MS); LC Column: Waters XBridge™ 30 mm×100 mm Sum; water w/0.1% formic acid; gradient: 28-62% acetonitrile w/0.1% formic acid in 1.35 minutes then 62-95% in 6.65 minutes, then held at 95% for 3.55 minutes. Column temperature: ambient; flow rate: 45 mL/minute) to yield the title compound as a colorless oil (55.3 mg, 130.6 µmol). MS (m/z): 446 (M+23).

Preparation 3

Diethyl (1S,2S,5R,6R)-2-amino-4-oxo-bicyclo[3.1.0]hexane-2,6-dicarboxylate

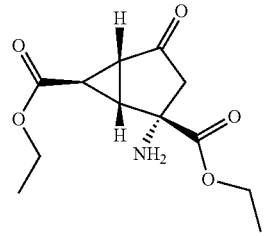 [SMILES: CCOC(=O)[C@H]1[C@@H]2C(=O)C[C@@](N)(C(=O)OCC)[C@@H]21]

Charge a 500 mL three neck flask equipped with a condenser, nitrogen inlet and a thermometer with ditert-butyl (1S,2S,5R,6R)-2-(tert-butoxycarbonylamino)-4-oxo-bicyclo[3.1.0]hexane-2,6-dicarboxylate (15 g, 36.4 mmol) in ethanol (365 mL). Add thionyl chloride (13.3 mL, 182.3 mmol) to a stirring solution at room temperature via syringe (small exotherm) then heat to reflux. After 24 hours cool the reaction to room temperature and concentrate in vacuo. Dissolve the residue in dichloromethane (50 mL) then concentrate on a rotary evaporator (repeat 3 times). Partition the residue between ethyl acetate (200 mL) and saturated sodium hydrogenate carbonate (150 mL). Wash the organic phase with brine (150 mL), dry over sodium sulfate, filter then concentrate to dryness to give the title compound as an oil (8.24 g, 32.3 mmol). MS (m/z): 256 (M+1).

Preparation 4

Diethyl (1S,2S,5R,6R)-2-acetamido-4-oxo-bicyclo[3.1.0]hexane-2,6-dicarboxylate

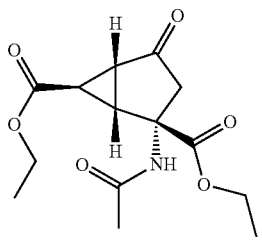 [SMILES: CCOC(=O)[C@H]1[C@@H]2C(=O)C[C@@](NC(C)=O)(C(=O)OCC)[C@@H]21]

Add acetic acid anhydride (5 mL, 50.8 mmol) to a stirred solution of diethyl (1S,2S,5R,6R)-2-amino-4-oxo-bicyclo[3.1.0]hexane-2,6-dicarboxylate (7.2 g, 28.2 mmol) and triethylamine (7.9 mL, 56.4 mmol) in dry dichloromethane (72 mL) at room temperature. After 2 hours, quench with water (100 mL) and stir vigorously for 20 minutes. Separate the dichloromethane layer via a hydrophobic frit and evaporate to a light brown oil (9.6 g). Purify by flash chromatography eluting with ethyl acetate:iso-hexane (70:30 to 90:10) to give the title compound as a pale yellow glass foaming on drying (6.53 g, 22 mmol). MS (m/z): 298 (M+1), 320 (M+23), 617 (2M+23).

Preparation 5

Diethyl (1S,2S,5R,6S)-2-acetamido-4-methylene-bicyclo[3.1.0]hexane-2,6-dicarboxylate

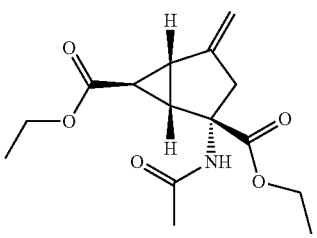 [SMILES: C=C1C[C@@](NC(C)=O)(C(=O)OCC)[C@H]2[C@@H]1[C@@H]2C(=O)OCC]

Charge an oven-dried 250 mL round-bottom flask with (methyl)triphenylphosphonium bromide (9.72 g, 26.7 mmol) and dry tetrahydrofuran (122 mL). Cool the suspension to 0 to −5° C. and treat with 2M sodium bis(trimethylsilyl)amide in tetrahydrofuran (13.3 mL, 26.7 mmol) in a dropwise manner Stir the resultant bright yellow mixture at 0° C. for 20 minutes then treat with a solution of diethyl (1S,2S,5R,6R)-2-acetamido-4-oxo-bicyclo[3.1.0]hexane-2,6-dicarboxylate (6.1 g, 20.5 mmol) in tetrahydrofuran (30 mL). Allow the reaction to warm slowly to room temperature over 3 hours. After stirring for 20 hours at room temperature quench with iced water (200 mL) and extract with ethyl acetate (200 mL). Wash extracts with water (100 mL), brine (100 mL), dry, filter and evaporate to dark brown oil. Add diethyl ether (70 mL) and iso-hexane (20 mL) and seed the solution with triphenylphosphine oxide. Allow to stand for 2 hours, decant the solution, add silica and concentrate under vacuum. Purify by flash chromatography eluting with ethyl acetate:iso-hexane (60:40 to 80:20) to give a pink oil (6.81 g) contaminated with triphenylphosphine oxide. Re-purify by flash chromatography eluting with ethyl acetate:iso-hexane (60:40) to give the title compound as a viscous yellow oil (3.98 g, 13.5 mmol). MS (m/z): 296 (M+1), 318 (M+23), 613 (2M+23).

Preparation 6

Diethyl (1S,2S,5R,6S)-2-acetamidospiro[bicyclo[3.1.0]hexane-4,1'-cyclopropane]-2,6-dicarboxylate

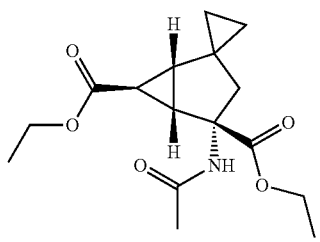 [SMILES: CCOC(=O)[C@H]1[C@H]2[C@@H]1[C@](NC(C)=O)(C(=O)OCC)CC21CC1]

Under nitrogen, add a solution of trifluoroacetic acid (1.9 mL, 25 mmol) in dichloromethane (12.5 mL) dropwise very slowly to a cooled (ice bath) stirred solution of diethylzinc (1M in heptanes) (25 mL, 25 mmol) in dichloromethane (12.5 mL). After 10 minutes, add a solution of diiodomethane (2.01 mL, 25 mmol) in dichloromethane (12.5 mL). After 10 minutes, add a solution of diethyl (1S,2S,5R,6S)-2-acetamido-4-methylene-bicyclo[3.1.0]hexane-2,6-dicarboxylate (2.46 g, 8.3 mmol) in dichloromethane (12.5 mL). After 60 minutes remove the ice bath and leave the reaction mixture to stir overnight at room temperature. Quench the clear reaction solution by dropwise addition of the reaction mixture to 0.2M aqueous hydrochloric acid (200 mL) under vigorous stirring. After 1 hour separate the dichloromethane layer, wash with brine, dry over magnesium sulfate, filter and concentrate in vacuum to yield the required product contaminated with unreacted starting material (4.4 g). Purify by flash chromatography eluting with ethyl acetate:cyclohexane (50:50 to 100:0) to give a colorless oil (3.1 g). Purify by SFC(RT=2.48 minutes (UV, 200 nm); HPLC Column: AD-H 30 mm×250 mm 5 μm; $CO_2$ gradient: 5% iso-propyl alcohol w/0.2% dimethylethylamine for 0.5 minutes, then 5%-27% in 2.2 minutes. Column temperature: 35° C.; pressure: 100000 kPa; flow rate: 210 mL/minute) to yield unreacted diethyl (1S,2S,5R,6S)-2-acetamido-4-methylene-bicyclo[3.1.0]hexane-2,6-dicarboxylate. (580 mg, 2.0 mmol) and title compound (1.82 g, 5.9 mmol). MS (m/z): 310 (M+1), 332 (M+23).

Preparation 7

Diethyl (1S,2S,5R,6S)-2-amino-4-methylene-bicyclo[3.1.0]hexane-2,6-dicarboxylate

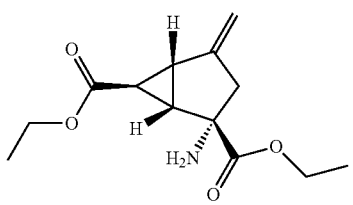 [SMILES: C=C1C[C@@](N)(C(=O)OCC)[C@H]2[C@@H]1[C@@H]2C(=O)OCC]

Method 1:

Prepare a solution of approximately 1M hydrogen chloride in ethanol by dropwise addition of trimethylsilyl chloride (13.8 mL, 108 mmol) to ethanol (110 mL). Dissolve ditert-butyl (1S,2S,5R,6S)-2-(tert-butoxycarbonylamino)-4-methylene-bicyclo[3.1.0]hexane-2,6-dicarboxylate (7.4 g, 18.1 mmol) in this acidic solution and heat to 60° C. for 16 hours. Evaporate to a viscous yellow oil, redissolve in water (50 mL) and filter the hazy solution to remove trace insolubles. Neutralize the aqueous acidic solution with sodium bicarbonate (8.4 g, 0.1 mol) and extract with dichloromethane (2×100 mL). Dry the combined dichloromethane solutions via a hydrophobic frit and evaporate to a pale yellow liquid (4.14 g). Purify by chromatography on amino-bonded silica eluting with ethyl acetate:iso-hexane (20:80 to 80:20) to give a colorless liquid (3.6 g). Repurify by chromatography on amino-bonded silica eluting with ethyl acetate:iso-hexane (20:80) to give a colorless liquid of the title product (2.81 g, 61%). MS (m/z): 254 (M+1).

Method 2:

Dry p-toluenesulphonic acid monohydrate (6.97 g, 36.6 mmol) in vacuo at 50° C. for 3 days. Add to a stirred solution of ditert-butyl (1S,2S,5R,6S)-2-(tert-butoxycarbonylamino)-4-methylene-bicyclo[3.1.0]hexane-2,6-dicarboxylate (5.0 g, 12.2 mmol) in ethanol (35.5 mL) and heat to 60° C. for 3 days. Remove solvent under reduced pressure to give a residue. Take up the residue into water (100 mL), make basic using sodium bicarbonate and extract with dichloromethane (3×100 mL). Dry the extracts over sodium sulfate, filter and then concentrate under reduced pressure to give an orange residue of the title compound (1.52 g, 51%). MS (m/z): 254 (M+1).

Preparation 8

Diethyl (1S,2S,5R,6S)-2-(9H-fluoren-9-ylmethoxycarbonylamino)-4-methylene-bicyclo[3.1.0]hexane-2,6-dicarboxylate

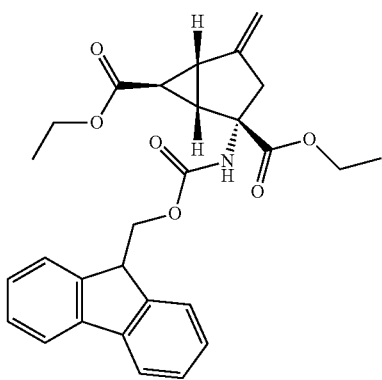 [SMILES: C=C1C[C@@](NC(=O)OCC2c3ccccc3-c3ccccc32)(C(=O)OCC)[C@H]2[C@@H]1[C@@H]2C(=O)OCC]

Add solid 9-fluorenylmethyl chloroformate (3.15 g, 12.2 mmol) portion wise over 5 minutes to a stirred solution of diethyl (1S,2S,5R,6S)-2-amino-4-methylene-bicyclo[3.1.0]hexane-2,6-dicarboxylate (2.8 g, 11.1 mmol) and sodium bicarbonate (2.04 g, 24.3 mmol) in tetrahydrofuran (28 mL) and water (8.4 mL) cooled to 0-5° C. After 1 hour, add water (10 mL) and extract with ethyl acetate (50 mL). Wash the extract with brine solution (20 mL), dry, filter and evaporate to a pale yellow oil (6.5 g). Purify by flash chromatography eluting with ethyl acetate:iso-hexane (10:90 to 20:80) to give a viscous colorless oil (4.58 g). Repurify by flash chromatography eluting with ethyl acetate:iso-hexane (20:80) to give a white semi-solid foam of title compound (4.22 g, 80%). MS (m/z): 476 (M+1).

Preparation 9

Diethyl (1S,2S,5R,6S)-2-(9H-fluoren-9-ylmethoxycarbonylamino)spiro[bicyclo[3.1.0]hexane-4,1'-cyclopropane]-2,6-dicarboxylate

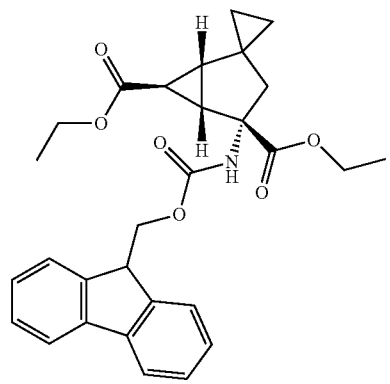 [SMILES: CCOC(=O)[C@H]1[C@H]2[C@@H]1[C@](NC(=O)OCC1c3ccccc3-c3ccccc31)(C(=O)OCC)CC21CC1]

Add a solution of trifluoroacetic acid (2.66 g, 23.3 mmol) in dichloromethane (11.7 mL) dropwise over 5 minutes to a stirred solution of diethyl zinc 1M in heptanes (23.3 mL, 23.3 mmol) in dichloromethane (11.7 mL) cooled to 0-5° C. under nitrogen (exothermic reaction). After 10 minutes, add a solution of diiodomethane (6.25 g, 23.3 mmol) in dichloromethane (11.7 mL). After 10 minutes, add a solution of diethyl (1S,2S,5R,6S)-2-(9H-fluoren-9-ylmethoxycarbonylamino)-4-methylene-bicyclo[3.1.0]hexane-2,6-dicarboxylate (3.70 g, 7.8 mmol) in dichloromethane (11.7 mL). After 2 hours at 0° C., allow to warm to room temperature and stir for 16 hours. Quench the reaction mixture with cold 0.5M hydrochloric acid (50 mL) and dichloromethane (20 mL) and stir vigorously. Separate the dichloromethane layer via a hydrophobic frit and then evaporate to a pale yellow oil. Purify by flash chromatography eluting with ethyl acetate:iso-hexane (10:90 to 20:80) to give a colorless oil (3.49 g). Repurify by flash chromatography eluting with ethyl acetate:iso-hexane (20:80) taking the centre cut fractions to give a colorless foam of title compound (2.12 g, 56%). MS (m/z): 490 (M+1). A second lot of product from the less pure fractions is obtained by repeated chromatography (363 mg, additional 9%).

Preparation 10

Diethyl (1S,2S,5R,6R)-2-benzyloxycarbonylamino-4-oxo-bicyclo[3.1.0]hexane-2,6-dicarboxylate

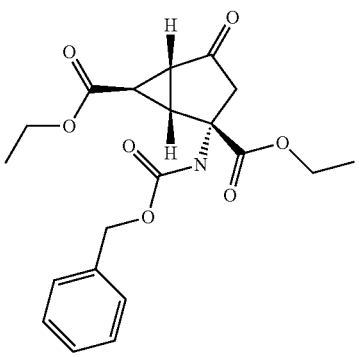 [SMILES: CCOC(=O)[C@H]1[C@@H]2C(=O)C[C@@](NC(=O)OCc3ccccc3)(C(=O)OCC)[C@@H]21]

Method 1:

Add dibenzyl dicarbonate (18.6 mL, 76.1 mmol) to a solution of diethyl (1S,2S,5R,6R)-2-amino-4-oxo-bicyclo[3.1.0]hexane-2,6-dicarboxylate (16.2 g, 63.5 mmol) in dichloromethane (500 mL) then add dropwise triethylamine (10.6 mL, 76.1 mmol). Stir the reaction mixture for 30 minutes before washing with 1N hydrochloric acid (200 mL). Wash the dichloromethane phase with brine, separate and concentrate in vacuo. Purify by flash chromatography eluting with ethyl acetate:iso-hexane (0:100 to 75:25) to yield the title compound (11.6 g, 47%). MS (m/z): 388 (M+1), 410 (M+23).

Method 2:

Add to a round bottom flask diethyl (1S,2S,5R,6R)-2-amino-4-oxo-bicyclo[3.1.0]hexane-2,6-dicarboxylate hydrochloride (226.86 g, 777.65 mmol), water (1.13 L) and tetrahydrofuran (1.13 L). Add slowly sodium bicarbonate (143.72 g, 1.71 mol) in 5 portions (observing $CO_2$ evolution and internal temperature from 31° C. to 25° C.). Add then a solution of benzyl chloroformate (120.6 mL, 855.42 mmol) in tetrahydrofuran (226.9 mL) and keep the internal temperature below 28° C. (10 minutes) stirring the reaction at 25° C. for 1 hour. Pour the mixture into methyl-t-butyl ether (1.25 L). Separate the layers, extract the aqueous with ethyl acetate (750 ml) and discard the aqueous phase. Wash the mixture with brine, dry over magnesium sulfate, filter and concentrate to dryness to give the title compound as a colorless oil (302.82 g, 777.65 mmol). MS (m/z): 388 (M+1).

Preparation 11

Diethyl (1S,2S,5R,6S)-2-benzyloxycarbonylamino-4-methylene-bicyclo[3.1.0]hexane-2,6-dicarboxylate

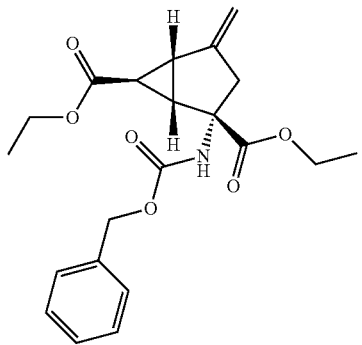 [SMILES: C=C1C[C@@](NC(=O)OCc2ccccc2)(C(=O)OCC)[C@H]2[C@@H]1[C@@H]2C(=O)OCC]

Method 1:

Charge an oven dried 500 mL round-bottom flask with (methyl)triphenylphosphonium bromide (15.4 g, 43.1 mmol) and dry tetrahydrofuran (112 mL). Cool the suspension to 0 to −5° C. and treat with 2M sodium bis(trimethylsilyl)amide in tetrahydrofuran (23 mL, 46 mmol) in a dropwise manner. Stir the resultant bright yellow suspension at 0° C. for 30 minutes then treat with a solution of diethyl (1S,2S,5R,6R)-2-benzyloxycarbonylamino-4-oxo-bicyclo[3.1.0]hexane-2,6-dicarboxylate (11.2 g, 28.8 mmol) in tetrahydrofuran (22.4 mL). Allow the reaction to slowly warm to room temperature. After 4 hours, quench with ice (120 g), brine (120 mL) and extract with ethyl acetate (250 mL). Wash the extracts with brine (2×100 mL), dry, filter and evaporate to a red oil. Redissolve in diethyl ether (100 mL) and add iso-hexane (80 mL) slowly in portions to precipitate triphenylphosphine oxide as a red semi-solid (5.2 g). Treat the solution with dry silica (~50 g) and concentrate to dryness. Purify by flash chromatography eluting with ethyl acetate:iso-hexane (20:80) to give the title compound as a colorless viscous oil (7.37 g, 66%). MS (m/z): 388 (M+1), 410 (M+23).

Method 2:

Add potassium tert-butoxide (104.72 g, 933.18 mmol) to a suspension of (methyl)triphenylphosphonium bromide (340.16 g, 933.18 mmol) in tetrahydrofuran (1.82 L) at room temperature (no change in internal temperature). Then add a solution of diethyl (1S,2S,5R,6R)-2-benzyloxycarbonylamino-4-oxo-bicyclo[3.1.0]hexane-2,6-dicarboxylate (302.82 g, 777.65 mmol) in tetrahydrofuran (1.82 L) maintaining the temperature at 24° C. Stir the mixture at 50° C. for 3 hours. Dilute the reaction with ethyl acetate (1.5 L), wash with water (2×3 L) and brine. Dry the organic phase over magnesium sulfate, filter and concentrate to afford a dark brown oil. Purify by flash chromatography eluting with ethyl acetate:hexanes (9:1) to give the title compound as a colorless oil (183.35 g, 473.25 mmol). MS (m/z). 388 (M+1), 410 (M+23).

Preparation 12

Diethyl (1S,2S,5R,6S)-2-benzyloxycarbonylamino-spiro[bicyclo[3.1.0]hexane-4,1'-cyclopropane]-2,6-dicarboxylate

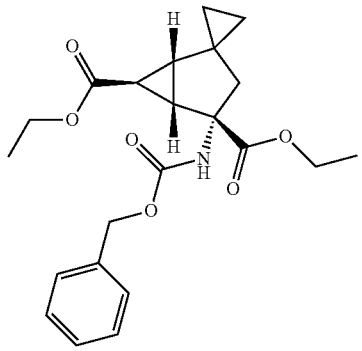 [SMILES: CCOC(=O)[C@H]1[C@H]2[C@@H]1[C@](NC(=O)OCc1ccccc1)(C(=O)OCC)CC21CC1]

Method 1:

Add a solution of 1M diethylzinc in heptanes (64.1 mL, 64.1 mmol) in dichloromethane (14.6 mL) dropwise slowly over 10 minutes to a stirred solution of trifluoroacetic acid (4.27 mL, 56.5 mmol) in dichloromethane (73 mL) cooled to 0-5° C. under nitrogen. After 10 minutes, add a solution of diiodomethane (4.6 mL, 56.5 mmol) in dichloromethane (14.6 mL). After 10 minutes, add a solution of diethyl (1S,2S,5R,6S)-2-benzyloxycarbonylamino-4-methylene-bicyclo[3.1.0]hexane-2,6-dicarboxylate (7.3 g, 18.8 mmol) in dichloromethane (14.6 mL). After 1 hour, remove the ice bath and leave the hazy solution to stir for 20 hours at room temperature. After 24 hours, quench the reaction mixture with iced 0.5M aqueous hydrochloric acid (160 mL, 80 mmol) and dichloromethane (200 mL) and stir the mixture vigorously. Separate the dichloromethane layer and then dry the dichloromethane phase filtering through 2 hydrophobic fits. Evaporate to a pale yellow oil turning brown overnight. Purify by flash chromatography eluting with ethyl acetate:iso-hexane (20:80) to give the title compound as a mixture with unreacted diethyl (1S,2S,5R,6S)-2-benzyloxycarbonylamino-4-methylene-bicyclo[3.1.0]hexane-2,6-dicarboxylate as a colorless oil (5.1 g).

Add a solution of trifluoroacetic acid (2.93 mL, 38.7 mmol) in dichloromethane (10 mL) dropwise slowly over 10 minutes to a stirred solution of diethylzinc 1M in heptanes (38.7 mL, 38.7 mmol) in dichloromethane (50 mL) cooled to 0-5° C. under nitrogen. After 10 minutes, add a solution of diiodomethane (3.12 mL, 38.7 mmol) in dichloromethane (10 mL) to the reaction mixture. After 10 minutes, add a solution of the mixture of olefin and diethyl (1S,2S,5R,6S)-2-benzyloxycarbonylaminospiro[bicycle[3.1.0]hexane-4,1'-cyclopropane]-2,6-dicarboxylate (5 g, 12.9 mmol) in dichloromethane (10 mL). After 1 hour remove the ice bath and leave the hazy solution to stir for 16 hours at room temperature. After 20 hours, quench the reaction mixture with iced 0.5M hydrogen chloride (140 mL, 70 mmol) and dichloromethane (160 mL) and stir the mixture vigorously. Wash the dichloromethane layer with 0.5M aqueous hydrochloric acid (100 mL), dry over sodium sulfate and then filter through 2 hydrophobic fits. Evaporate to a pale yellow oil (5.89 g). Purify by flash chromatography eluting with ethyl acetate: iso-hexane (15:85 to 25:75) to give the title compound as a colorless oil (4.28 g) contaminated with a small amount of reactant.

Redissolve in acetone (40 mL), water (20 mL), sodium bicarbonate (0.54 g, 6.45 mmol) and magnesium sulfate (0.78 g, 6.45 mmol). Cool to 0° C. and add potassium permanganate (0.2 g, 1.29 mmol) to give a bright purple mixture. After 3 hours at room temperature, quench with solid sodium thiosulfate pentahydrate (0.32 g, 1.29 mmol) and filter the suspension through a pad of diatomaceous earth, washing through with acetone. Evaporate to a small volume, dilute with water (20 mL) and extract with ethyl acetate (60 mL). Wash the extracts with brine, dry, filter and evaporate to an oil. Purify by flash chromatography eluting with ethyl acetate: iso-hexane (15:85 to 25:75) to give the title compound as a colorless oil (3.62 g, 70%). MS (m/z): 402 (M+1).

Method 2:

Add a solution of 1M diethylzinc in heptanes (1.6 L, 1.6 mol) via cannula to dichloromethane (870.9 mL) at 0° C. (bath temperature −5° C.), then add slowly a solution of trifluoroacetic acid (121.02 mL, 1.6 mol) in dichloromethane (870.9 mL) maintaining the temperature below 3° C. After 1 hour of addition stir the mixture for 5 minutes then add diiodomethane (130.3 mL, 1.6 mol) in one portion and stir for 15 minutes. Add a solution of diethyl (1S,2S,5R,6S)-2-benzyloxycarbonylamino-4-methylene-bicyclo[3.1.0]hexane-2,6-dicarboxylate (183.35 g, 449.58 mmol) in dichloromethane (348.4 mL) over 10 minutes and stir the mixture at room temperature overnight. Cool to 0° C., quench with 0.5M hydrochloric acid (1.5 L) and stir the mixture vigorously. Separate the organic layer, wash with brine and concentrate to dryness. Dissolve in water (733.4 mL) and acetone (733.4 mL), cool to 0° C. then add magnesium sulfate (81.17 g, 674.37 mmol), sodium bicarbonate (56.65 g, 674.37 mmol) followed by potassium permanganate (28.42 g, 179.83 mmol). Stir the mixture at room temperature. After 30 minutes add sodium thiosulfate pentahydrate (197.10 g, 311.03 mmol) followed by diatomaceous earth (100 g). Stir for 30 minutes and filter through a pad of diatomaceous earth. Wash the pad with methyl-t-butyl ether and extract the aqueous layer with methyl-t-butyl ether. Dry the organic layer over magnesium sulfate, filter and concentrate in vacuo. Purify by flash chromatography eluting with hexanes: methyl-t-butyl ether (10:90 to 50:50) to yield the title compound as a colorless oil (92.67 g, 51%). $^1$H NMR (CDCl$_3$) δ: 0.39-0.52 (m, 1H), 0.55-0.78 (m, 3H), 1.25 (broad t, J=7.1 Hz, 6H), 1.58 (broad dd, J=2.9 and 6.3 Hz, 1H), 1.64-1.73 (m, 1H), 1.95 (broad t, J=2.9 Hz, 1H), 2.03-2.17 (m, 1H), 2.52 (dd, J=2.7 and 6.3 Hz, 1H), 4.09 (q, J=7.1 Hz, 2H), 4.16-4.32 (m, 2H), 5.08 (broad s, 2H), 5.44 (broad s, 1H), 7.28-7.41 (m, 5H).

Also obtain diethyl (1S,2S,5R,6S)-2-(benzyloxycarbonyl (methyl)amino)spiro[bicyclo[3.1.0]hexane-4,1'-cyclopropane]-2,6-dicarboxylate as a by-product (22.67 g, 5.46 mmol). $^1$H NMR (CDCl$_3$) δ: 0.37-0.52 (m, 1H), 0.54-0.80 (m, 3H), 1.26 (broad t, J=7.1 Hz, 6H), 1.55-1.68 (m, 1H), 1.64-1.73 (m, 1H), 1.70-1.80 (m, 1H), 1.97 (broad t, J=3.1 Hz, 1H), 2.30 (dd, J=3.1 and 6.3 Hz, 1H), 3.16 (s, 3H), 3.99-4.29 (m, 4H), 5.09 (broad s, 2H), 7.38-7.62 (m, 5H).

Preparation 13

Diethyl (1S,2S,5R,6S)-2-aminospiro[bicyclo[3.1.0] hexane-4,1'-cyclopropane]-2,6-dicarboxylate

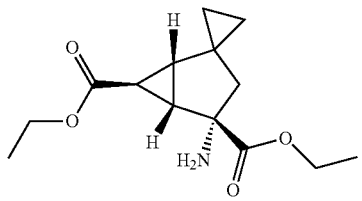 [SMILES: CCOC(=O)[C@H]1[C@H]2[C@@H]1[C@](N)(C(=O)OCC)CC21CC1]

Method 1:

Add piperidine (3.16 g, 37.2 mmol) to a stirred solution of diethyl (1S,2S,5R,6S)-2-(9H-fluoren-9-ylmethoxycarbonylamino)spiro[bicyclo[3.1.0]hexane-4,1'-cyclopropane]2,6-dicarboxylate (2.10 g, 4.29 mmol) in dichloromethane (10.5 mL) at room temperature. After 30 minutes, evaporate to a yellow solid. Purify by flash chromatography eluting with ethyl acetate:iso-hexane (30:70 to 80:20) to first elute 1-(9H-fluoren-9-ylmethyl)-piperidine and then to elute a pale yellow liquid of title compound (1.07 g, 93%). MS (m/z): 268 (M+1).

Method 2:

Dissolve diethyl (1S,2S,5R,6S)-2-benzyloxycarbonylaminospiro[bicyclo[3.1.0]hexane-4,1'-cyclopropane]-2,6-dicarboxylate (3.62 g, 9 mmol) in ethanol (54 mL) and add solution to 10% palladium on carbon (Degussa type E101 NE/W, 0.18 g, 0.17 mmol). Hydrogenate on Parr equipment for 4 hours at 345 kPa. Filter the reaction through a pad of diatomaceous earth to remove the catalyst, wash with ethanol and evaporate to a colorless oil as the title compound (2.23 g, 93%). MS (m/z): 268 (M+1).

Preparation 14

Diethyl (1S,2S,5R,6S)-2-[[(2S)-2-(tert-butoxycarbonylamino)propanoyl]amino]spiro[bicyclo[3.1.0]hexane-4,1'-cyclopropane]-2,6-dicarboxylate

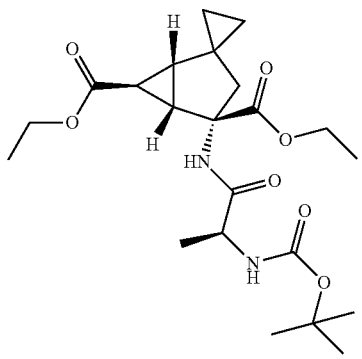 [SMILES: CCOC(=O)[C@H]1[C@H]2[C@@H]1[C@](NC(=O)[C@H](C)NC(=O)OC(C)(C)C)(C(=O)OCC)CC21CC1]

Combine diethyl (1S,2S,5R,6S)-2-aminospiro[bicyclo[3.1.0]hexane-4,1'-cyclopropane]-2,6-dicarboxylate (1.92 g, 7.17 mmol), (2S)-2-(tert-butoxycarbonylamino)propanoic acid (1.92 g, 10 mmol), 4-dimethylaminopyridine (9 mg, 717 μmol) and 1-hydroxybenzotriazole (1.36 g, 10 mmol) in dichloromethane (48 mL). Add triethylamine (1.5 mL, 10.8 mmol) and 1-(3-dimethylaminopropyl)-3-ethylcarbodiimide hydrochloride (1.92 g, 10 mmol) and stir for 2 hours at room temperature under a nitrogen atmosphere. Dilute the reaction with ethyl acetate (200 mL), water (50 mL) and brine (50 mL). Stir vigorously then separate the ethyl acetate layer, wash with 0.2M hydrochloric acid (50 mL), water (50 mL), saturated sodium hydrogen carbonate (50 mL) and brine (50 mL). Dry, filter and concentrate the solution to give a yellow oil (3.48 g). Purify by flash chromatography eluting with ethyl acetate:iso-hexane (15:85 to 25:75) then (25:75 to 40:60) to give the material as an oil. Redissolve in dichloromethane, concentrate and dry under vacuum to give the title compound as a white foamy material (3.05 g, 6.95 mmol). MS (m/z): 461 (M+23).

The following compounds are prepared essentially by the method of preparation 14.

Preparation 17

(1S,2S,5R,6S)-2-[[(2S)-2-(tert-Butoxycarbonylamino)propanoyl]amino]spiro[bicyclo[3.1.0]hexane-4,1'-cyclopropane]-2,6-dicarboxylic acid Method 1:

Add a solution of 2M lithium hydroxide in water (27.8 mL, 55.6 mmol) to a cold stirred solution of diethyl (1S,2S,5R,

| Prep. No. | Chemical name | Structure | Physical data |
|---|---|---|---|
| 15 | Diethyl (1S,2S,5R,6S)-2-[[(2S)-2-(tert-butoxycarbonylamino)-4-methylsulfanyl-butanoyl]amino]spiro[bicyclo[3.1.0]hexane-4,1'-cyclopropane]-2,6-dicarboxylate | 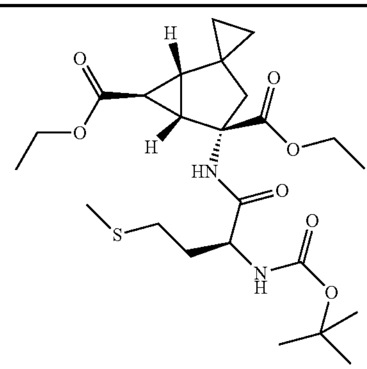 | MS (m/z): 499 (M + 1), 521 (M + 23) |
| 16 | Diethyl (1S,2S,5R,6S)-2-[[2-(tert-butoxycarbonylamino)acetyl]amino]spiro[bicyclo[3.1.0]hexane-4,1'-cyclopropane]-2,6-dicarboxylate | 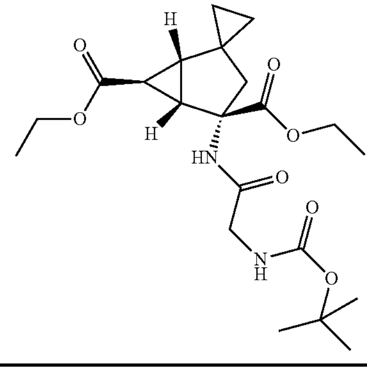 | MS (m/z): 447 (M + 23). |

6S)-2-[[(2S)-2-(tert-butoxycarbonylamino)propanoyl]amino]spiro[bicyclo[3.1.0]hexane-4,1'-cyclopropane]-2,6-dicarboxylate (3.05 g, 6.9 mmol) in tetrahydrofuran (36 mL) under nitrogen. Stir the bilayer solution at room temperature for 20 hours. Acidify with 2M hydrochloric acid (29 mL), ice (~20 g) and extract with ethyl acetate (100 mL). Wash the extracts with brine (50 mL), dry on sodium sulfate, filter and evaporate to a white semi-solid foam. Redissolve the material in hot ethyl acetate (15 mL). Filter and dry the material under vacuum to give the title compound as a white solid (2.06 g, 5.4 mmol). MS (m/z): 405 (M+23).

separate the phases. Wash the organic layer with more water (300 mL). Acidify the combined aqueous layers to pH=2-3 with 1N potassium hydrogen sulfate and then extract with ethyl acetate. Dry the organic layer over magnesium sulfate, filter and evaporate under vacuum. Dissolve the crude in tetrahydrofuran (600 mL) and heat to reflux. Add heptane (2.1 L) and cool the solution. Filter the solid and dry under vacuum to give the title compound as a white solid (149 g, 98%). MS (m/z): 405 (M+23).

The following compounds are prepared essentially by the method 1 of preparation 17.

| Prep No. | Chemical name | Structure | Physical data |
|---|---|---|---|
| 18 | (1S,2S,5R,6S)-2-[[(2S)-2-(tert-Butoxycarbonylamino)-4-methylsulfanyl-butanoyl]amino]spiro[bicyclo[3.1.0]hexane-4,1'-cyclopropane]-2,6-dicarboxylic acid | 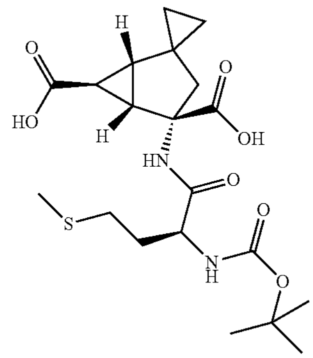 [SMILES: CSCC[C@H](NC(=O)OC(C)(C)C)C(=O)N[C@@]1(C(=O)O)CC2(CC2)[C@H]2[C@H](C(=O)O)[C@H]21] | MS (m/z): weak 465 (M + 23) |
| 19 | (1S,2S,5R,6S)-2-[[2-(tert-Butoxycarbonylamino)acetyl]amino]spiro[bicyclo[3.1.0]hexane-4,1'-cyclopropane]-2,6-dicarboxylic acid | 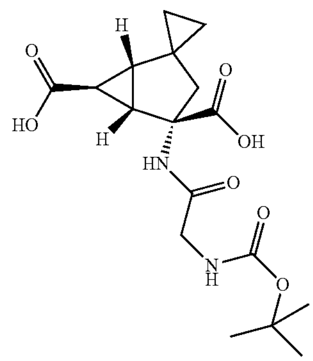 [SMILES: CC(C)(C)OC(=O)NCC(=O)N[C@@]1(C(=O)O)CC2(CC2)[C@H]2[C@H](C(=O)O)[C@H]21] | MS (m/z): 391 (M + 23), |

Method 2:

Dissolve diethyl (1S,2S,5R,6S)-2-benzyloxycarbonylaminospiro[bicyclo[3.1.0]hexane-4,1'-cyclopropane]-2,6-dicarboxylate (159 g, 396.05 mmol) in ethanol (792.1 mL), and add 10% palladium on carbon (15.9 g, 14.94 mmol) followed by a 37.5% wt/wt hydrochloric acid solution in water (6.62 mL, 79.21 mmol). Hydrogenate on a 2 L Parr equipment at 413 kPa at room temperature. After 4 hours filter the mixture through diatomaceous earth and a glass microfiber filter (Whatman) and concentrate in vacuo. Dissolved the crude in tetrahydrofuran (396 mL), add chlorodimethoxytriazine (74.50 g, 415.86 mmol) and (2S)-2-(tert-butoxycarbonylamino) propanoic acid (79.88 g 415.86 mmol). Cool this mixture to 0° C. and add N-methylmorpholine (131.06 mL, 1.19 mol). Stir the mixture at room temperature. After 5 hours filter the crude through diatomaceous earth and wash the cake with tetrahydrofuran (200 mL). Remove the solvent partially under vacuum and cool the resulting orange solution to 0° C. Add 2M sodium hydroxide in water (792.1 mL, 1.58 mol) dropwise. Stir the mixture overnight, allowing the reaction to reach room temperature. Add dichloromethane (1 L) and Preparation 20

Diethyl (1S,2S,5R,6S)-2-(tert-butoxycarbonylamino)spiro[bicyclo[3.1.0]hexane-4,1'-cyclopropane]-2,6-dicarboxylate

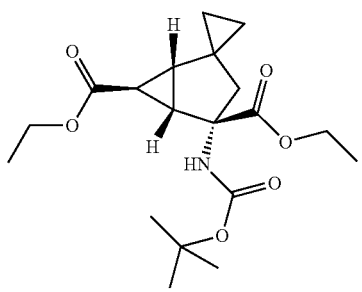 [SMILES: CCOC(=O)[C@H]1[C@H]2[C@@H]1[C@](NC(=O)OC(C)(C)C)(C(=O)OCC)CC21CC1]

Method 1:

To a solution of diethyl (1S,2S,5R,6S)-2-aminospiro[bicyclo[3.1.0]hexane-4,1'-cyclopropane]-2,6-dicarboxylate (0.47 g, 722.38 µmol) in dichloromethane (5 mL) add polymer supported diiso-propyl-ethylamine (1.02 g, 3.61 mmol) followed by di-t-butyldicarbonate (0.41 g, 1.88 mmoles) in dichloromethane (6.00 mL) and stir the reaction mixture at room temperature overnight. Add additional di-t-butyldicarbonate (0.32 g, 1.36 mmole) stir for a further 2 hours. Dilute with ethanol (20 mL) and purify by SCX-2 ion exchange resin cartridge (10 g) pretreated with 2 column volumes of ethanol. After loading the cartridge wash with 4 column volumes of ethanol before concentrating the eluent in vacuo to yield the crude product (808 mg). Purify the crude material by flash chromatography eluting with ethyl acetate:cyclohexane (0:100 to 40:60) to yield the desired material (100 mg). Flush the cartridge with 2 column volumes of 3M ammonia in methanol to yield a yellow solid (430 mg) of unreacted crude diethyl (1S,2S,5R,6S)-2-aminospiro[bicyclo[3.1.0]hexane-4,1'-cyclopropane]-2,6-dicarboxylate. Add di-t-butyldicarbonate (0.32 g, 1.44 mmol) to the recovered diethyl (1S,2S,5R,6S)-2-aminospiro[bicyclo[3.1.0]hexane-4,1'-cyclopropane]-2,6-dicarboxylate in tetrahydrofuran (20 mL), stir at room temperature overnight. Add then triethylamine (201.37 µL, 1.44 mmol) and additional di-t-butyldicarbonate (0.32 g, 1.44 mmol) and maintain stirring for 72 hours. Add excess triethylamine (201.37 µL, 1.44 mmol), di-t-butyldicarbonate (0.32 g, 1.44 mmol) and catalytic N,N-dimethyl 4-aminopyridine (40.93 µmol) and stir overnight. Dilute with ethanol (30 mL) and purify the solution by SCX-2 ion exchange resin cartridge (10 g) pretreated with 2 column volumes of ethanol. Wash with 4 column volumes of ethanol and concentrate the solution in vacuo to yield 757 mg of crude desired product. Purify by flash chromatography eluting with ethyl acetate:cyclohexane (0:100 to 40:60) to yield a second fraction of the desired title product (24 mg). Combine both fractions to yield the title compound (337.47 µmol, 47%). MS (m/z): 390 (M+23), 757 (2M+23).

Method 2:

Add di-t-butyldicarbonate (0.88 g, 4.01 mmol) to a solution of diethyl (1S,2S,5R,6S)-2-aminospiro[bicyclo[3.1.0]hexane-4,1'-cyclopropane]-2,6-dicarboxylate (1.4 g, 5.24 mmol) in tetrahydrofuran (30 mL) and stir the reaction mixture at room temperature overnight under nitrogen. Filter through a hydrophobic fit, wash colorless gel, with ethyl acetate. Concentrate the combined organics layers in vacuo to give a colorless oil. Purify by flash chromatography eluting with ethyl acetate:iso-hexane (0:100 to 30:70) to yield 1.82 g of oil. Dry further under high vacuum to yield the title compound (1.79 g, 93%). MS (m/z): 390 (M+23), 757 (2M+23).

Preparation 21

(1S,2S,5R,6S)-2-(tert-Butoxycarbonylamino)spiro[bicyclo[3.1.0]hexane-4,1'-cyclopropane]-2,6-dicarboxylic acid

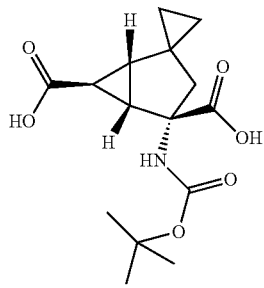 [SMILES: CC(C)(C)OC(=O)N[C@@]1(C(=O)O)CC2(CC2)[C@H]2[C@H](C(=O)O)[C@H]21]

Add diethyl (1S,2S,5R,6S)-2-(tert-butoxycarbonylamino)spiro[bicyclo[3.1.0]hexane-4,1'-cyclopropane]-2,6-dicarboxylate (1.79 g, 4.87 mmol) in tetrahydrofuran (29.2 mL) to a freshly prepared solution of lithium hydroxide monohydrate (1.64 g, 38.97 mmol) in water (19.5 mL) and stir overnight at 60° C. Dilute with water (30 mL), extract with ethyl acetate (2×50 mL). Separate aqueous and organic layers. Wash organic layer with 2M hydrochloric acid. Wash the aqueous layer with 2M hydrochloric acid (25 mL) then extract with ethyl acetate (2×50 mL). Combine the organic layers and wash with brine (15 mL). Dry on magnesium sulfate, filter and concentrate to dryness. Redissolve in dichloromethane and concentrate to dryness to give the title compound (1.49 g, 98%). MS (m/z): 334 (M+23).

Preparation 22

Dibenzyl (1S,2S,5R,6S)-2-(tert-butoxycarbonylamino)spiro[bicyclo[3.1.0]hexane-4,1'-cyclopropane]-2,6-dicarboxylate

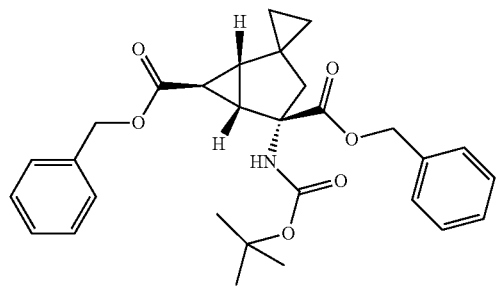 [SMILES: CC(C)(C)OC(=O)N[C@@]1(C(=O)OCc2ccccc2)CC2(CC2)[C@H]2[C@H](C(=O)OCc3ccccc3)[C@H]21]

Add cesium carbonate (0.24 g, 730.7 µmol) and benzyl bromide (87.16 µL, 730.7 µmol) to a solution of (1S,2S,5R,6S)-2-(tert-butoxycarbonylamino)spiro[bicyclo[3.1.0]hexane-4,1'-cyclopropane]-2,6-dicarboxylic acid (0.09 g, 292.29 µmol) in N,N-dimethylformamide (2 mL). Stir at room temperature for 1.5 hours under nitrogen. Quench with water and extract with ethyl acetate. Separate the layers and filter the organics through a hydrophobic frit before concentrating to dryness to yield the crude product (134 mg). Purify by flash chromatography eluting with ethyl acetate:iso-hexane (1:99 to 25:75) to give a clear oil. Purify further by flash chromatography eluting with ethyl acetate:iso-hexane (1:99 10:90) to yield the title product (105 mg, 68%) as a clear oil. MS (m/z): 514 (M+23).

The following compound is prepared essentially by the method of preparation 22.

| Prep No. | Chemical name | Structure | Physical data |
|---|---|---|---|
| 23 | bis[(2-fluorophenyl)methyl] (1S,2S,5R,6S)-2-(tert-butoxycarbonylamino)-spiro[bicyclo[3.1.0]hexane-4,1'-cyclopropane]-2,6-dicarboxylate | 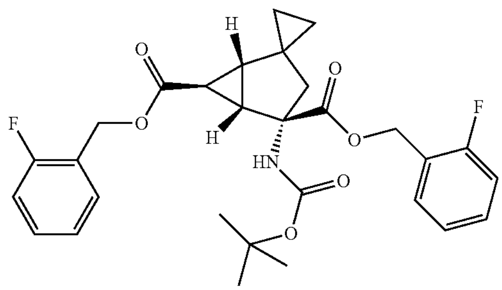 [SMILES: CC(C)(C)OC(=O)N[C@@]1(C(=O)OCc2ccccc2F)CC2(CC2)[C@H]2[C@H](C(=O)OCc3ccccc3F)[C@H]21] | MS (m/z): 550 (M + 23) |

EXAMPLE 1

(1S,2S,5R,6S)-2-Aminospiro[bicyclo[3.1.0]hexane-4,1'-cyclopropane]-2,6-dicarboxylic acid hydrochloride

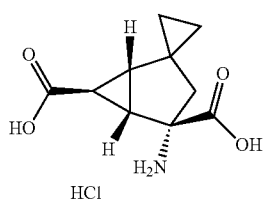 [SMILES: N[C@@]1(C(=O)O)CC2(CC2)[C@H]2[C@H](C(=O)O)[C@H]21 ; Cl]

HCl

Charge a 5 mL ReactiVial with ditert-butyl (1S,2S,5R,6S)-2-(tert-butoxycarbonylamino)spiro[bicyclo[3.1.0]hexane-4,1'-cyclopropane]-2,6-dicarboxylate (55 mg, 129.8 µmol). To this add a 5N aqueous hydrochloric acid solution (3 mL; 20.8 mmol) and 1,4-dioxane (1 mL). Stir the mixture at 90° C. for one hour. Seal the ReactiVial and continue stirring at 90° C. for 3 hours. Cool to ambient temperature and stand for 3 days. Concentrate under reduced pressure to a dark solid. Prepare a Oasis® HLB Waters (1 g) cartridge by washing with 2 column volumes of methanol, followed by 6 column volumes of water. Dissolve the dark solid in water and load onto the cartridge. Wash the cartridge with water (2 column volumes) and collect the eluent. Freeze-dry the solution to yield title compound (16.1 mg, 65 µmol). MS (m/z): 212 (M+1). $^1$H NMR (D$_2$O) δ 0.45 (m, 1H), 0.53 (m, 1H), 0.64 (m, 1H), 0.74 (m, 1H), 1.72-1.78 (m, 2H) 1.86 (d, J=14.2 Hz, 1H), 2.07 (m, 1H), 2.37 (m, 1H).

EXAMPLE 2

(1S,2S,5R,6S)-2-Aminospiro[bicyclo[3.1.0]hexane-4,1'-cyclopropane]-2,6-dicarboxylic acid

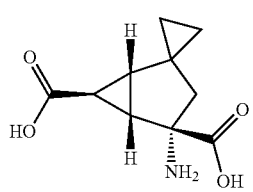 [SMILES: N[C@@]1(C(=O)O)CC2(CC2)[C@H]2[C@H](C(=O)O)[C@H]21]

Add 2M sodium hydroxide (11.5 mL, 23.1 mmol) with diethyl (1S,2S,5R,6S)-2-acetamidospiro[bicyclo[3.1.0]hexane-4,1'-cyclopropane]-2,6-dicarboxylate (1.19 g, 3.8 mmol). Upon addition heat the reaction mixture to reflux under a blanket of nitrogen. After 21 hours add excess 2M sodium hydroxide (5.8 mL, 11.5 mmol) and resume heating for 120 hours. Purify by cation exchange chromatography (Dowex™ 50X8-100) as follows. Filter any insoluble particles and rinse with HPLC grade water. Concentrate the solution by half. Load the solution onto the resin, allowing to flow through the column at a drip rate of about 1 drop every 1-2 seconds. After the initial loading volume has dropped to the resin surface, rinse the resin with HPLC grade water (~1 to 2 column volumes) and repeat 3 times. Monitor the pH of the effluent and pursue rinsing with HPLC grade water until application complete (return of pH back to pH=7.). Once the complete pH cycle has been observed and the effluent has returned to pH=7, wash the column with at least one column volume each of HPLC grade water, HPLC grade water: tetrahydrofuran (1:1), then HPLC grade water. Displace the product from the resin with 10% pyridine: HPLC grade water and continue elution with 10% pyridine: HPLC grade water until no additional product was detected by TLC. Combine the fractions containing the desired material, concentrate to dryness to give a white solid. Freeze-dry to yield the title compound (795 mg, 3.8 mmol). MS (m/z): 212 (M+1). $^1$H NMR (D$_2$O+5% d$_5$-pyridine) δ: 0.38 (m, 1H), 0.45 (m, 1H), 0.55 (m, 1H), 0.69 (m, 1H), 1.50 (dd, J=2.9 Hz, 1H), 1.62 (d, J=13.7 Hz, 1H), 1.78 (m, 2H), 2.11 (dd, J=2.9 Hz, 1H).

EXAMPLE 3

(1S,2S,5R,6S)-2-[[(2S)-2-Aminopropanoyl]amino] spiro[bicyclo[3.1.0]hexane-4,1'-cyclopropane]-2,6-dicarboxylic acid; 1,4-dioxane (1:0.5); hydrochloride

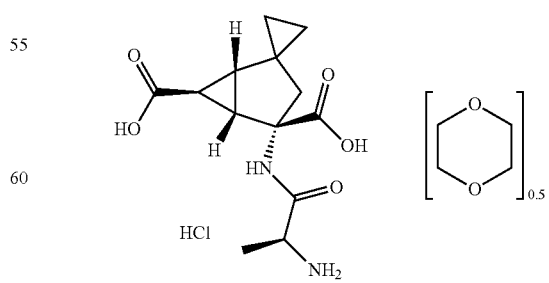

Add a solution of 4M hydrogen chloride in 1,4-dioxane (1.57 mL, 6.3 mmol) to a stirred suspension of (1S,2S,5R, 6S)-2-[[(2S)-2-(tert-butoxycarbonylamino) propanoyl]amino]spiro[bicyclo[3.1.0]hexane-4,1'-cyclopropane]-2,6-dicarboxylic acid (0.16 g, 418.4 μmol) in 1,4-dioxane (1.6 mL) at room temperature under nitrogen. After 16 hours filter a white solid, wash with 1,4-dioxane, dry in vacuum at 60° C. overnight to yield the title compound (0.14 g): MS (m/z): 283 (M+1). $^1$H NMR (D$_2$O) δ 0.46 (m, 1H), 0.65 (m, 1H), 1.47 (d, J=7 Hz, 3H), 1.70 (dd, J=2.7 Hz, 1H), 1.81 (q, J=15 Hz, 2H), 1.87 (broad t, J=2.7 and 2.9 Hz, 1H), 2.65 (dd, J=2.7 and 2.9 Hz, 1H), 3.68 (s, 4H), 4.00 (q, J=7 Hz, 1H), 4.70 (m, 2H).

EXAMPLE 4

(1S,2S,5R,6S)-2-[[(2S)-2-Aminopropanoyl]amino]spiro[bicyclo[3.1.0]hexane-4,1'-cyclopropane]-2,6-dicarboxylic acid

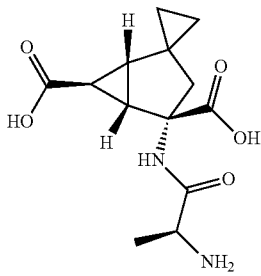 [SMILES: C[C@H](N)C(=O)N[C@@]1(C(=O)O)CC2(CC2)[C@H]2[C@H](C(=O)O)[C@H]21]

Add concentrated hydrochloric acid (36.94 mL, 430.11 mmol) to a solution of (1S,2S,5R,6S)-2-[[(2S)-2-(tert-butoxycarbonylamino)propanoyl]amino]spiro[bicyclo[3.1.0]hexane-4,1'-cyclopropane]-2,6-dicarboxylic acid (82.24 g, 215.06 mmol) in acetone (822.4 mL), and stir the mixture at 50° C. After 1.5 hours cool the mixture to 0° C. and add 50% sodium hydroxide in water to pH=3.6-3.8. Stir the solid obtained for 1 hour, filter and wash with water. Dry under vacuum for 48 hours to yield the title compound as a white solid (36 g, 127.53 mmol). MS (m/z): 283 (M+1).

EXAMPLE 5

(1S,2S,5R,6S)-2-[[(2S)-2-Aminopropanoyl]amino]spiro[bicyclo[3.1.0]hexane-4,1'-cyclopropane]-2,6-dicarboxylic acid hydrochloride

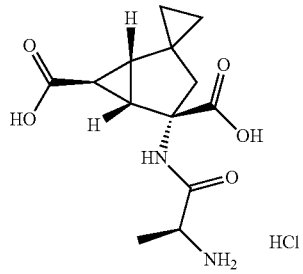 [SMILES: C[C@H](N)C(=O)N[C@@]1(C(=O)O)CC2(CC2)[C@H]2[C@H](C(=O)O)[C@H]21 ; Cl]

Add 4M hydrogen chloride in 1,4-dioxane (20 mL, 80 mmol) to a stirred suspension of (1S,2S,5R,6S)-2-[[(2S)-2-(tert-butoxycarbonylamino) propanoyl]amino]spiro[bicyclo[3.1.0]hexane-4,1'-cyclopropane]-2,6-dicarboxylic acid (2.06 g, 5.4 mmol) in 1,4-dioxane (21 mL) at room temperature under nitrogen. Sonicate the reaction mixture few minutes and then maintain stirring 16 hours. Filter the solid, wash with 1,4-dioxane, dry in vacuum at 60° C. for 6 hours to give 2.2 g of white solid. Redissolve the material in HPLC grade water (20 mL), filter to remove any insoluble particles and freeze-dry the filtrate to yield title compound (1.51 g, 4.75 mmol). MS (m/z): 283 (M+1). $^1$H NMR (D$_2$O) δ 0.46 (m, 1H), 0.65 (m, 1H), 1.46 (d, J=7.1 Hz, 3H), 1.69 (dd, J=2.9 Hz, 1H), 1.81 (q, J=14.3 Hz, 2H), 1.87 (broad t, J=2.9 Hz, 1H), 2.65 (dd, J=2.9 Hz, 1H), 4.00 (q, J=7.02 Hz, 1H), 4.70 (m, 2H).

The following compounds are prepared essentially by the method of Example 4.

| Ex. No. | Chemical name | Structure | Physical data |
|---|---|---|---|
| 6 | (1S,2S,5R,6S)-2-[[(2S)-2-Amino-4-methylsulfanyl-butanoyl]amino]spiro[bicyclo[3.1.0]hexane-4,1'-cyclopropane]-2,6-dicarboxylic acid hydrochloride | 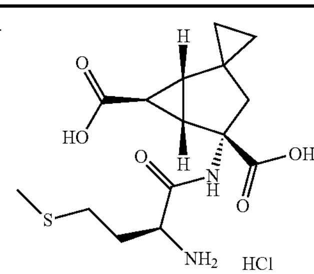 | MS (m/z): 343 (M + 1) |
| 7 | (1S,2S,5R,6S)-2-[(2-Aminoacetyl)amino]spiro[bicyclo[3.1.0]hexane-4,1'-cyclopropane]-2,6-dicarboxylic acid hydrochloride | 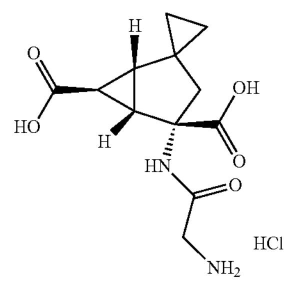 [SMILES: NCC(=O)N[C@@]1(C(=O)O)CC2(CC2)[C@H]2[C@H](C(=O)O)[C@H]21 ; Cl] | MS (m/z): 269 (M + 1) |

EXAMPLE 8

Dibenzyl (1S,2S,5R,6S)-2-aminospiro[bicyclo[3.1.0] hexane-4,1'-cyclopropane]-2,6-dicarboxylate; 1,4-dioxane; hydrochloride

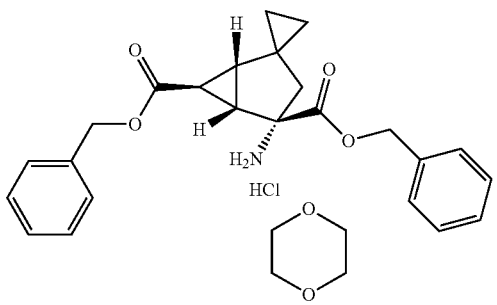 [SMILES: N[C@@]1(C(=O)OCc2ccccc2)CC2(CC2)[C@H]2[C@H](C(=O)OCc3ccccc3)[C@H]21 ; Cl ; C1COCCO1]

Add 4M hydrogen chloride in 1,4-dioxane (493.30 µL, 1.97 mmol) to a stirred suspension of dibenzyl (1S,2S,5R, 6S)-2-(tert-butoxycarbonylamino)spiro[bicyclo[3.1.0]hexane-4,1'-cyclopropane]-2,6-dicarboxylate (0.1 g, 0.2 mmol) in 1,4-dioxane (970 µL) at room temperature under nitrogen and stir for 20 hours. Add excess 4M hydrogen chloride solution in 1,4-dioxane (493.30 µL, 1.97 mmol) and heat to 80° C. Concentrate to dryness, triturate with acetonitrile and freeze-dry the suspension to give the title compound as a white solid (89.9 mg, 88%) as a (1:1) adduct with 1,4-dioxane. MS (m/z): 392 (M+1).

EXAMPLE 9

Bis[(2-fluorophenyl)methyl](1S,2S,5R,6S)-2-amino-spiro[bicyclo[3.1.0]hexane-4,1'-cyclopropane]-2,6-dicarboxylate hydrochloride

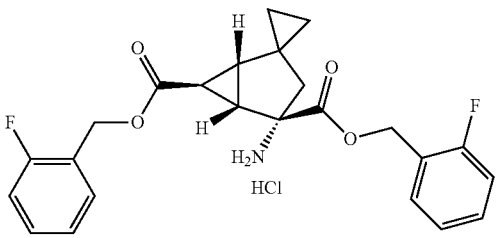 [SMILES: N[C@@]1(C(=O)OCc2ccccc2F)CC2(CC2)[C@H]2[C@H](C(=O)OCc3ccccc3F)[C@H]21 ; Cl]

Add 4M hydrogen chloride solution in 1,4-dioxane (4.64 mL, 18.58 mmol) to a stirred solution of bis[(2-fluorophenyl) methyl](1S,2S,5R,6S)-2-(tert-butoxycarbonylamino)spiro [bicyclo[3.1.0]hexane-4,1'-cyclopropane]-2,6-dicarboxylate (0.98 g, 1.86 mmol) in 1,4-dioxane (4.64 mL) at room temperature under nitrogen and stir the solution for 20 hours. Concentrate in vacuo to give an oil (0.93 g). Dissolve in a mixture of acetonitrile (10 mL), water (30 mL) and freeze dry over the weekend to give a white solid (820 mg) as a mixture of title compound contaminated with (1S,2S,5R,6S)-2-amino-2-[(2-fluorophenyl)methoxycarbonyl]spiro[bicyclo [3.1.0]hexane-4,1'-cyclopropane]-6-carboxylic acid (~7-10%). MS (m/z): 320 (M+H). Dissolve the white solid in acetonitrile (8 mL) to yield a translucent solution. Allow to stand for 1 hour, before filtering. Concentrate the filtrate in vacuo to yield a sticky foam. Redissolve in ethyl acetate, wash with a saturated solution of sodium hydrogen carbonate, dry over magnesium sulfate, filter and concentrate in vacuo to yield 774 mg. Redissolve in diethyl ether (11 mL), add 1M hydrogen chloride in diethyl ether (1.86 mL, 1.86 mmol), concentrate in vacuo to yield a white solid foam. Dry further overnight in vacuo at 50° C. to yield the title compound (0.74 g, 85%). MS (m/z): 428 (M+1), 450 (M+23).

EXAMPLE 10

(1S,2S,5R,6S)-2-[[(2S)-2-Aminopropanoyl]amino] spiro[bicyclo[3.1.0]hexane-4,1'-cyclopropane]-2,6-dicarboxylic acid dihydrate

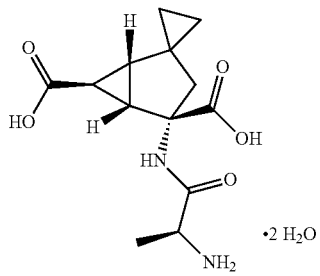 [SMILES: C[C@H](N)C(=O)N[C@@]1(C(=O)O)CC2(CC2)[C@H]2[C@H](C(=O)O)[C@H]21 ; "·2 H2O"]

Step 1: Diethyl (1S,2S,5R,6R)-2-amino-4-oxo-bicyclo[3.1.0]hexane-2,6-dicarboxylate hydrochloride

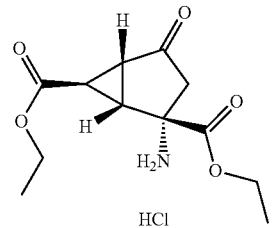 [SMILES: CCOC(=O)[C@H]1[C@@H]2C(=O)C[C@@](N)(C(=O)OCC)[C@@H]21 ; Cl]

Under a nitrogen atmosphere, add acetyl chloride (86.5 mL, 1.2 mol) to absolute ethanol (1.0 L, 17.2 mol) drop-wise while maintaining the internal reaction temperature below 30° C. Stir the resulting mixture for 15 minutes and add di-t-butyl (1S,2S,5R,6R)-2-(tert-butoxycarbonylamino)-4-oxo-bicyclo[3.1.0]hexane-2,6-dicarboxylate (100 g, 0.24 mol) in one portion. Heat the resulting mixture to reflux for 16-20 hours. Concentrate the reaction mixture to an oil under reduced pressure. Dissolve the crude product in methylene chloride (250 mL) and concentrate in vacuo. Repeat the methylene chloride/concentration process to afford a white foam. Add ethyl acetate (150 mL) and heat the mixture to 65° C. Add methyl t-butyl ether (100 mL) and stir the mixture at 65° C. for 15 minutes. Add methyl t-butyl ether (300 mL) over 15 minutes, stir at 65° C. for 15 minutes, then shut heat and allow the slurry to cool to ambient temperature. Filter the mixture and wash the filter cake with methyl t-butyl ether (150 mL). Transfer the cake to a vacuum oven and dry overnight at 25° C. to afford the crude product (67.5 g). Transfer the solids to a round bottom flask, dilute with ethyl acetate (170 mL) and heat the mixture to 65° C. Stir the mixture for 1 hour, add tetrahydrofuran (68 mL) and ethanol (3 mL). Shut heat source and add methyl t-butyl ether (272 mL) over 20 minutes, allowing the mixture to cool to ambient temperature. Filter the slurry, wash the cake with 95/5 methyl t-butyl ether/ethyl acetate (2×75 mL) and further dry the solids in a vacuum oven overnight at 25° C. to afford the title compound as a white solid (60.0 g, 98.0%). MS (m/z): 256 (M+1).

Step 2: Diethyl (1S,2S,5R,6R)-2-benzyloxycarbonylamino-4-oxo-bicyclo[3.1.0]hexane-2,6-dicarboxylate

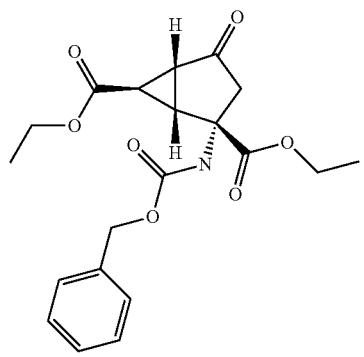 [SMILES: CCOC(=O)[C@H]1[C@@H]2C(=O)C[C@@](NC(=O)OCc3ccccc3)(C(=O)OCC)[C@@H]21]

Suspend diethyl-(1S,2S,5R,6R)-2-amino-4-oxo-bicyclo[3.1.0]hexane-2,6-dicarboxylate-hydrochloride (55.0 g, 188.5 mmol) in tetrahydrofuran (220 mL), then add water (220 mL) and potassium carbonate (92.1 g, 659.9 mmol). Stir the resulting mixture for 30 minutes. Add benzyl chloroformate (26.7 mL, 175.3 mmol) to the mixture over 45 minutes, keeping the reaction temperature below 25° C. Stir reaction mixture for 30 minutes, then dilute with ethyl acetate (550 mL) and water (275 mL). Separate the phases and back extract the aqueous layer with ethyl acetate (250 mL). Combine the organics and wash it sequentially with aqueous HCl (0.5N, 100 mL), saturated NaHCO₃ (100 mL) and brine (100 mL). Dry the organic solution over Na₂SO₄, filter and concentrate in vacuo to afford the title compound as a clear oil (67.6 g, 92.1%). ¹H NMR (CDCl₃) δ 1.24-1.26 (m, 6H), 2.36 (bs, 1H), 2.47 (dd, 1H), 2.78 (dd, 1H), 2.90 (dd, 1H), 4.09-4.19 (m, 4H), 5.08 (s, 2H), 5.73 (s, 1H), 7.24-7.36 (m, 5H).

Step 3: Diethyl (1S,2S,5R,6S)-2-benzyloxycarbonylamino-4-methylene-bicyclo[3.1.0]hexane-2,6-dicarboxylate

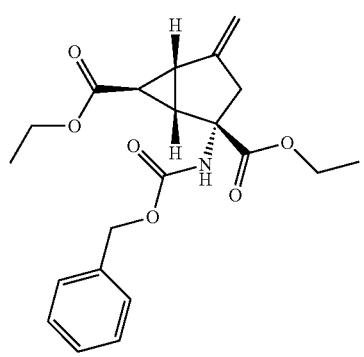 [SMILES: C=C1C[C@@](NC(=O)OCc2ccccc2)(C(=O)OCC)[C@H]2[C@@H]1[C@@H]2C(=O)OCC]

Under a nitrogen atmosphere, combine methyl-triphenylphosphonium bromide (67.4 g, 184.9 mmol) and tetrahydrofuran (300 mL) with agitation. Add a solution of potassium tert-butoxide (1M) in tetrahydrofuran, 184.9 mL, 184.9 mmol) to the reaction mixture over 15 minutes and stir the resulting slurry at ambient temperature for 3 hours. Dissolve diethyl (1S,2S,5R,6R)-2-benzyloxycarbonylamino-4-oxo-bicyclo[3.1.0]hexane-2,6-dicarboxylate (12.3 kg, 31.6 mol) in tetrahydrofuran (120 mL) and add to the reaction mixture over 1 hour, maintaining the reaction temperature below 30° C. Stir the resulting slurry overnight at ambient temperature, then dilute with ethyl acetate (600 mL) and quench with water (300 mL). After stirring the biphasic mixture for 30 minutes, separate the layers and wash the organics with water (300 mL) followed by 0.25M HCl (300 mL). Dry the organics over Na₂SO₄, filter, and concentrate in vacuo (45° C.) to afford the crude product as a dark oil (111.0 g). Purify the material by silica gel plug chromatography (1 Kg Kieselgel-60, 4 L 15% EtOAc in heptanes, then 10 L 30% EtOAc in heptanes) to afford the title compound as a clear oil (37.3 g, 87.9% potency, 54.9%). MS (m/z): 388 (M+1).

Step 4: Diethyl (1S,2S,5R,6S)-2-benzyloxycarbonylaminospiro[bicyclo[3.1.0]hexane-4,1'-cyclopropane]-2,6-dicarboxylate

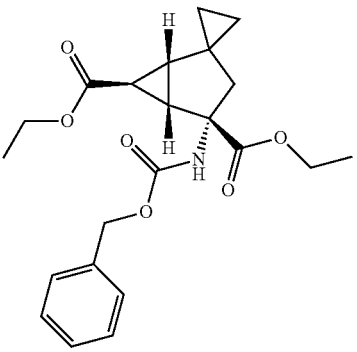 [SMILES: CCOC(=O)[C@H]1[C@H]2[C@@H]1[C@](NC(=O)OCc1ccccc1)(C(=O)OCC)CC21CC1]

To a jacketed reaction flask connected to a chiller unit, add diethylzinc solution (157.2 mL, 157.2 mmol, 1M in heptanes) under a nitrogen atmosphere. Cool the solution to −15° C. and dilute with cold (−15° C.), dry dichloroethane (157.2 mL). Dissolve trifluoroacetic acid (11.1 mL, 146.7 mmol) in dichloroethane (11.1 mL) and add to the reaction vessel over 50 minutes, keeping the internal temperature below −10° C. Stir the resulting suspension at −10 to −15° C. for 30 minutes. Dissolve diiodomethane (12.7 mL, 42.1 g, 157.2 mmol) in dichloroethane (12.7 mL) and add to the reaction mixture over 50 minutes, keeping the internal temperature below −10° C. Stir the resulting thin, white suspension at −10 to −15° C. for 30 minutes. Dissolve diethyl (1S,2S,5R,6S)-2-benzyloxycarbonylamino-4-methylene-bicyclo[3.1.0]hexane-2,6-dicarboxylate (20.3 g, 87.9% potency, 46.0 mmol) in dichloroethane (30.4 mL) and add to the reaction mixture over 10 minutes, keeping the internal temperature below −10° C. Stir the clear, pale yellow solution at −10° C. for 5 minutes and monitor for latent exotherms. Change the set point on the chiller to 0° C. and stir the reaction mixture at that temperature for 48 hours. Quench the reaction mixture by addition of 5N HCl (62.9 mL, 314.4 mmol) over 15 minutes, keeping the internal temperature below 6° C. Stir the resulting mixture at 0-5° C. for 20 minutes, then transfer to a funnel and separate the layers. Wash the organic layer with 1N HCl (2×50 mL) followed by 1:1 saturated NaHCO₃/H₂O (60 mL), 1:1 saturated Na₂CO₃/H₂O (60 mL) and water (50 mL). Dry the organics over Na₂SO₄ and concentrate in vacuo to afford the title compound as a pale yellow oil (19.6 g, 60.3% potent, 63.9% corrected yield). ¹H NMR (DMSO-d₆) δ 0.37 (m, 2H), 0.52-0.55 (dm, 2H), 1.13-1.17 (m, 6H), 1.49-1.50 (m, 1H), 1.51-1.56 (m, 1H), 1.60-1.79 (m, 2H), 3.97-4.10 (m, 5H), 5.00 (s, 2H), 7.29-7.34 (m, 5H), 8.04 (s, 1H).

Step 5: Diethyl (1S,2S,5R,6S)-2-aminospiro[bicyclo[3.1.0]hexane-4,1'-cyclopropane]-2,6-dicarboxylate hydrochloride

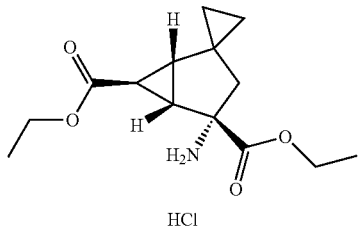 [SMILES: CCOC(=O)[C@H]1[C@H]2[C@@H]1[C@](N)(C(=O)OCC)CC21CC1 ; Cl]

Charge absolute ethanol (100 mL, 10 volumes), concentrate. HCl (2.1 mL, 1.0 N) and diethyl (1S,2S,5R,6S)-2-benzyloxycarbonylaminospiro[bicyclo[3.1.0]hexane-4,1'-cyclopropane]-2,6-dicarboxylate (9.7 g, 24.16 mmol) to a HEL reactor followed by Pd black (3.9 g, 40 wt %). Purge the reactor three times with nitrogen followed by three hydrogen purges and pressurization to 40 psi hydrogen. Allow the reaction to stir between 20-30° C. for at least two hours until the completion of the reaction monitored by HPLC. Filter the resulting slurry through a pad of Hyflo Super Cel® and wash the wet cake with absolute ethanol (2×30 mL, 3 volumes). Transfer the filtrate to a clean reactor and displace ethanol with isopropyl acetate to approximately 5 volumes based on in-situ product yield from calibration curve. Cool the resulting slurry to 0-5° C. over at least 3 hours. Filter the resulting slurry and wash the wet cake washed with cold isopropyl acetate (3×5 mL, 0.5 volumes). Dry under reduced pressure at 30° C. for at least 12 hours to provide the title compound (4.66 g, 15.34 mmol 63.5%) $^1$H NMR (DMSO-$d_6$, 400 MHz): δ 8.84 (s, 3H), 4.31-4.15 (m, 2H), 4.03 (q, J=7.0, 2H), 2.42 (dd, J=3.1, 2.6, 1H), 2.24 (dd, J=6.2, 2.6, 1H), 1.94 (d, J=14.1, 1H), 1.68 (d, J=14.1, 1H), 1.63 (dd, J=6.6, 3.1, 1H), 1.25 (t, J=7.0, 3H), 1.17 (t, J=7.0, 3H), 0.77-0.71 (m, 1H), 0.65-0.59 (m, 1H), 0.56-0.51 (m, 1H), 0.50-0.44 (m, 1H).

Step 6: Diethyl (1S,2S,5R,6S)-2-[[(2S)-2-(tert-butoxycarbonylamino)propanoyl]amino]spiro[bicyclo[3.1.0]hexane-4,1'-cyclopropane]-2,6-dicarboxylate

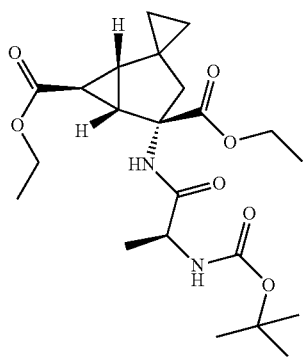 [SMILES: CCOC(=O)[C@H]1[C@H]2[C@@H]1[C@](NC(=O)[C@H](C)NC(=O)OC(C)(C)C)(C(=O)OCC)CC21CC1]

Charge tetrahydrofuran (45 mL, 10 volumes) and (2S)-2-(tert-butoxycarbonylamino)propanoic acid (3.4 g, 1.2 equivalents) to a reactor followed by N-methylmorpholine (1.96 mL, 1.2 equivalents) and 2-chloro-4,6-dimethoxy-1,3,5-triazine (3.12 g, 1.2 equivalents). Stir the resulting thin slurry between 20-25° C. for at least 3 hours until the reaction is complete by HPLC. Charge diethyl (1S,2S,5R,6S)-2-aminospiro[bicyclo[3.1.0]hexane-4,1'-cyclopropane]-2,6-dicarboxylate hydrochloride (4.55 g, 14.81 mmol) in one portion between 20-25° C. followed by N-methylmorpholine (1.63 mL, 1.0 equivalents) over at least 10 minutes keeping the temperature between 20-25° C. Stir the resulting slurry between 20-25° C. for at least 2 hours until the reaction is complete by HPLC. Filter the resulting solids and wash the wet cake with tetrahydrofuran (2×10 mL, 2.2 volumes) to provide the title compound assuming 100% yield. Use the pale amber tetrahydrofuran solution of the title compound without further purification assuming a 100% yield. $^1$H NMR (DMSO-$d_6$, 400 MHz): δ 8.46 (s, 1H), 6.72 (d, J=7.9, 1H), 4.08-3.92 (m, 5H), 2.42-2.37 (m, 1H), 1.81-1.64 (m, 3H), 1.47 (dd, J=6.6, 3.1, 1H), 1.34 (s, 9H), 1.18-1.08 (m, 9H), 0.66-0.59 (m, 1H), 0.57-0.52 (m, 1H), 0.46-0.36 (m, 2H).

Step 7: (1S,2S,5R,6S)-2-[[(2S)-2-(tert-Butoxycarbonylamino)propanoyl]amino]spiro[bicyclo[3.1.0]hexane-4,1'-cyclopropane]-2,6-dicarboxylic acid

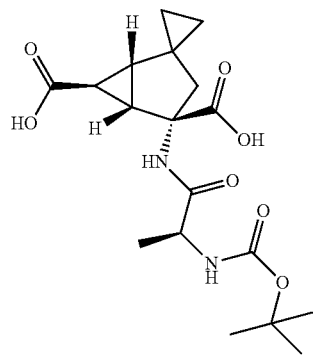 [SMILES: C[C@H](NC(=O)OC(C)(C)C)C(=O)N[C@@]1(C(=O)O)CC2(CC2)[C@H]2[C@H](C(=O)O)[C@H]21]

Charge 2 N NaOH (37 mL, 5.0 equivalents) and diethyl (1S,2S,5R,6S)-2-[[(2S)-2-(tert-butoxycarbonylamino)propanoyl]amino]spiro[bicyclo[3.1.0]hexane-4,1'-cyclopropane]-2,6-dicarboxylate (6.50 g, 14.81 mmol) to a reactor and allow to stir for at least 12 hours between 20-30° C. until the reaction is complete by HPLC. Transfer the reaction to a separatory funnel and allow it to settle for at least 10 minutes. Separate the phases and return the lower aqueous layer to the reactor. Add ethyl acetate (90 mL, 13.8 volumes) to the mixture, and then add 1 N NaHSO$_4$ until pH reaches 2 to 2.5. Separate layers and wash the organic with water (45 mL, 6.9 volumes). Remove water in organic phase atmospheric distillation with ethyl acetate to remove residual water. Cool the resulting slurry between 20-30° C. over at least 2 hours and allowed to granulate at that temperature for at least 90 minutes. Filter the resulting solids and wash the wet cake with ethyl acetate (3×15 mL, 2.3 volumes). Dry under reduced pressure at 45° C. to provide the title compound as a white solid (4.45 g, 11.64 mmol, 78.6%) $^1$H NMR (DMSO-$d_6$, 400 MHz, 50° C.): δ 12.01 (s, 2H), 8.22 (s, 1H), 6.49 (bs, 1H), 4.00 (bs, 1H), 2.43 (dd, J=6.5, 2.8, 1H), 1.83 (d, J=14.0, 1H), 1.68-1.62 (m, 2H), 1.42 (dd, J=6.5, 2.8, 1H), 1.36 (s, 9H), 1.15 (d, J=7.1, 3H), 0.67-0.61 (m, 1H), 0.56-0.51 (m, 1H), 0.46-0.36 (m, 2H).

Step 8: (1S,2S,5R,6S)-2-[[(2S)-2-Aminopropanoyl]amino]spiro[bicyclo[3.1.0]hexane-4,1'-cyclopropane]-2,6-dicarboxylic acid dihydrate

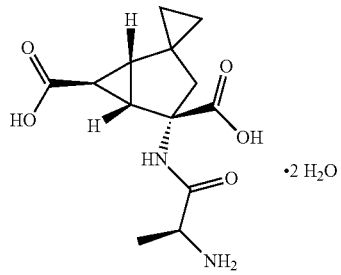 [SMILES: C[C@H](N)C(=O)N[C@@]1(C(=O)O)CC2(CC2)[C@H]2[C@H](C(=O)O)[C@H]21]

Charge water (32 mL, 8 volumes) and (1S,2S,5R,6S)-2-[[(2S)-2-(tert-butoxy carbonylamino)propanoyl]amino]spiro[bicyclo[3.1.0]hexane-4,1'-cyclopropane]-2,6-dicarboxylic acid (3.99 g, 10.4 mmol) to a reactor followed by concentrated HCl (1.80 mL, 2.0 equivalents) and then heat the reaction to 45-55° C. until the reaction complete (monitor by HPLC). Cool the reaction mixture to 20-30° C. and adjust the pH to approximately 3.6 with 5 N NaOH. Add absolute ethanol (15 mL, 3.75 volumes) over at least 30 minutes between 20-30° C. to the resulting slurry. Allow the resulting slurry to granulate between 20-30° C. for at least 12 hours. Cool the mixture between −5-5° C. and allow it to granulate for at least 60 minutes. Filter the resulting solids and wash the cake with 30% absolute ethanol in water (2×9 mL, 2.25 volumes). Dry the solids under reduced pressure at 35° C. for at least 12 hours, and then allow the resulting solids to stay on the balance until no additional weight change for at least 2 hours to provide the title compound as a white solid (2.71 g, 8.51 mmol, 81.6%). $^1$H NMR (D$_2$O, 400 MHz): δ 3.90 (q, J=7.2, 1H), 2.56 (dd, J=6.5, 2.9, 1H), 1.74-1.66 (m, 2H), 1.62-1.54 (m, 2H), 1.39 (d, J=7.1, 3H), 0.61-0.56 (m, 1H), 0.55-0.49 (m, 1H), 0.40-0.30 (m, 2H).

The X-ray powder diffraction (XRD) patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. The diffraction pattern were adjusted based on NIST 675 standard peaks at 8.85 and 26.77 degrees 2-theta. It is well known in the crystallography art that, for any given crystal form, the relative intensities of the diffraction peaks may vary due to preferred orientation resulting from factors, such as crystal habit, and the angular peak positions may vary slightly. For example, peak positions can shift due to a variation in the temperature or humidity at which a sample is analyzed, sample displacement. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns are collected at ambient temperature and relative humidity.

Thus, a prepared sample of Example 10 is characterized by an XRD pattern using CuKa radiation as having diffraction peaks (2-theta values) as described in Table 1 below. Specifically the pattern contains a peak at 5.20 in combination with one or more of the peaks selected from the group consisting of 10.45, 11.70, 15.75, 21.06 and 23.59 with a tolerance for the diffraction angles of 0.2 degrees.

TABLE 1

| X-ray powder diffraction peaks of Example 10 | | |
|---|---|---|
| Peak | Angle (2-Theta °) | Intensity (%) |
| 1 | 5.20 | 100 |
| 2 | 10.45 | 43.9 |
| 3 | 11.70 | 23.8 |
| 4 | 13.09 | 24.1 |
| 5 | 15.75 | 45.9 |
| 6 | 16.80 | 56.4 |
| 7 | 20.49 | 15.3 |
| 8 | 21.06 | 79.3 |
| 9 | 23.58 | 96 |
| 10 | 26.44 | 20.9 |

The mGlu receptors are G-protein-coupled receptors that modulate neuronal excitability. More particularly, altered glutamate neurotransmission has been linked to neurological disorders such as chronic pain conditions including persistent pain, neuropathic pain, chronic inflammatory pain, or visceral pain; psychiatric disorders, such as schizophrenia, bipolar disorder, generalized anxiety disorder, or post traumatic stress disorder; or neurogenerative disorders.

Since the compounds of the present invention are mGlu2/3 agonists, they may be suitable for treating the aforementioned conditions.

Human mGlu2 and mGlu3 Agonist FLIPR Assay

AV-12 cell lines, derived from Syrian Hamster fibroblasts and stably expressing the human mGlu2 or mGlu3 receptor and co-transfected with the rat glutamate transporter EAAT 1 (Excitatory Amino Acid Transporter 1) and the Gα15 subunit, are used for these studies. The expression of Gα15 allows Gi-coupled receptors to signal through the phospholipase C pathway, resulting in the ability to measure receptor activation by a fluorometric calcium response assay. The cell lines are maintained by culturing in Dulbecco's Modified Eagle's Medium (DMEM) with high glucose and pyridoxine hydrochloride supplemented with 5% dialyzed fetal bovine serum, 1 mM sodium pyruvate, 10 mM HEPES (4-(2-hydroxyethyl)-1-piperazineethanesulfonic acid), 1 mM of L-glutamine, and 5 µg/mL blasticidin (all media are purchased from Invitrogen). Confluent cultures are passaged biweekly using an enzyme-free dissociation solution (Chemicon S-004-B). Cells are harvested 24 hours prior to assay and dispensed using a Matrix Well-Mate cell seeder at 85,000 (mGlu2) or 115,000 (mGlu3) cells per well into 96-well, black-walled, poly-D-lysine-coated plates (BD BioCoat #354640) in medium containing only 250 (mGlu2) or 125 (mGlu3) µM L-glutamine (freshly added). Intracellular calcium levels are monitored before and after the addition of compounds using a Fluorometric Imaging Plate Reader (FLIPR, Molecular Devices). The assay buffer is comprised of Hank's Buffered Salt Solution (HBSS; Sigma) supplemented with 20 mM HEPES. The medium is removed and the cells are incubated with 8 µM Fluo-3AM (Molecular Probes, F-1241; 50 µL per well) in assay buffer for 90 minutes (mGlu2) or 120 minutes (mGlu3) at 25° C. The dye solution is removed and replaced with fresh assay buffer (50 µL per well). A single-addition FLIPR assay generating an 11-point concentration response curve (3× dilutions starting at 10 μM) for the agonist glutamate (Fisher A125-100) is conducted prior to each experiment to confirm the typical $EC_{50}$ response. Results are analyzed using Prism v4.03 (GraphPad Software). Compounds of the invention are tested in a single-addition FLIPR assay using a 10-point concentration response profile using 3× dilutions starting at a final concentration of 25 μM. Compounds of the invention are solubilized as 10 mM stocks in 0.1N NaOH and stored at −20 C. They are diluted through a three-fold dilution series into assay buffer. After taking an initial 5-sec fluorescent read on the FLIPR instrument, a compound of the invention is added to the cell plate (50 μL per well). Data are collected every second for the first 30 seconds and then every 3 seconds for a total of 90 seconds in order to detect agonist activity. The maximal response is defined as that induced by ECmax (100 μM glutamate). The compound effect is measured as maximal minus minimal peak heights in relative fluorescent units (RFUs) corrected for basal fluorescence measured in the absence of glutamate. Determinations are carried out using single plates. Agonist effects are quantified as percent stimulation induced by compound alone relative to the maximal glutamate response. All data are calculated as relative $EC_{50}$ values using a four-parameter logistic curve fitting program (ActivityBase v5.3.1.22).

Example 2 is measured in the hmGlu2 FLIPR assay run substantially as above to have an $EC_{50}$ of 39.0 nM±5.9 (n=3, error calculated as SEM). Example 2 is also measured in the hmGlu3 FLIPR assay run substantially as above to have an $EC_{50}$ of 285 nM±52.5 (n=8, error calculated as SEM). These results demonstrate that Example 2 is a potent mGlu2 and mGlu3 agonist.

Reversal of Persistent Pain Induced by Formalin Injection

The administration of formalin into plantar surface of the rat hind paw results in two phases of nocifensive behavior (such as licking, biting, and flinching of the injected paw): an early phase during approximately the 5 minutes after formalin administration and a late phase from approximately minute 10 through minute 60 after formalin injection. A quiescent period from approximately minute 5 to minute 10 separates the two phases. The scoring of these formalin-induced behaviors can be automated using startle chambers (SR-Lab, San Diego Instruments, San Diego, Calif.) which detects movements of the rats by means of an accelerometer. A test compound (active) is dosed (intraperitoneal route) in non-fasted male Sprague-Dawley rats within a range of 0.3-10 mg/kg 1 hour prior to the injection of intraplantar formalin. The rats are then individually placed in cylinders within the test chambers for acclimation. A test compound (prodrug) is orally dosed within a range of 0.45-15 mg/kg, in non-fasted male Sprague-Dawley rats two hours prior to the injection of intraplantar formalin. The rats are then individually placed in cylinders within the test chambers for acclimation. At specified time points, the rats are removed from the cylinders and administered formalin (50 μL of a 5% solution in saline) subcutaneously into the plantar surface of the right hind paw and immediately placed back into the cylinders. The cylinders are positioned on the load cells of the detection system within the test chambers, thereby allowing for the response to be monitored continuously for 60 minutes in 1-second bins. The number of nocifensive events [the number of 1-second bins with >20-load units] is totaled in 5-minute intervals. The 20-load unit threshold is large enough to eliminate the inclusion of normal physiological events such as breathing or sniffing, but of a significant magnitude to detect nocifensive events. Data are converted determining the number of events over threshold (20 load units) in each 1 second time bin over the 60 minutes of data collection. The early phase score is the sum of events greater than 20 load units from Time 0 to 5 minutes. The late-phase score is obtained by adding the total number events greater than 20 load units from Minute 11 to Minute 40 of the data collection period. Formalin data are evaluated by one-way analysis of variance (ANOVA) and the appropriate contrasts analyzed by Dunnett's 't' test for two-sided comparisons using JMP (v 6.0.2) statistical analysis program (SAS Institute Inc, Cary, N.C.). Differences are considered to be significant if the p-value is less than 0.05. $ED_{50}$ calculations are performed using non-linear regression curve fitting on percent reversal transformed data for each dose.

Example 2 is measured in this assay, run substantially as above, to have an $ED_{50}$ of 0.7 mg/kg (i.p.). Example 10 is measured in this assay, run substantially as above, to have an $ED_{50}$ of 4.8 mg/kg (p.o.). These results demonstrate that compounds within the scope of the present invention are useful medications for persistent pain.

Reversal of L5/L6 Nerve Ligation Induced Tactile Allodynia

Unilateral ligation of nerves innervating the hind leg region will result in a chronic persistent pain manifested as tactile allodynia in rats. L5/L6 nerve ligation is performed (Kim et al. *Pain* (1992) 50, 355-363). Neuropathic injury is produced by tightly ligating the left L5 and L6 spinal nerves under gaseous anesthesia with a mixture of isoflurane (3% for induction and 2% for maintenance) and oxygen. After a minimum of 14 days after surgery, tactile allodynia is evaluated by measuring tactile sensitivity of the injured paw to von Frey filaments with incremental bending forces (0.3 to 15 g) (Chaplan et al. *J. of Neuroscience Methods* (1994) 53, 55-63). Rats are considered to be hypersensitive when they demonstrate tactile allodynia (paw withdrawal in response to the application of a bending force of less than 2 grams). Baseline values are determined immediately prior to assessment of test compound. A test compound (prodrug) is orally dosed at 15 mg/kg and the tactile threshold for paw withdrawal is measured at 1, 2 and 4 hours post dosing. Data are expressed as response threshold in grams (g) and values are with standard errors of means (±SE mean) for each time point. Data are analyzed using an analysis of variance followed by a Dunnett's post hoc analysis and represent absolute change in pain threshold (Cmax=maximum Response Baseline) and expressed as Mean [log (maximum response)–log predose score)] (g).

Example 10 dosed orally at 15 mg/kg (wherein n=8; error calculated as SEM) is measured in this assay, run substantially as above, to have significantly increased mechanical threshold at one, two and four hours: 9.06±2.26, 12.31±1.86 and 8.63±1.98, respectively, as compared to the corresponding values after vehicle treatment: 1.50±0.60, 1.34±0.75, and 2.35±0.62 at one, two and four hours respectively. These results demonstrate that compounds within the scope of the present invention are useful medications for neuropathic pain conditions.

Reversal of CFA-Induced Mechanical Hyperalgesia

Induction of local inflammation in the rat hind paw will cause a persistent mechanical hyperalgesia that can be measured by determining the threshold to pressure stimuli to give a painful response. The method for complete Freund's adjuvant (CFA) induced mechanical hyperalgesia in rats is largely described in Iadarola et al. *Brain Res.* (1988) 455, 205-212. Rats are placed under isoflurane anesthesia while the right paw is injected with 50 μl of CFA (Sigma C5881, 1 mg/ml mycobacterium extract in 85% paraffin oil, 15% mannide monooleate) intraplantar. Animals are allowed to recover in soft bedding cages and mechanical hyperalgesia changes measured 24 hours post-CFA injection. Mechanical hyperalgesia (Randall Sellito Test) is determined by gently restraining the rat and placing the paw between the plinth and pusher (Ugo Basile Analgesy-meter). The gram force when the animal withdraws the paw is recorded. A maximal force of no more than 250 grams is applied and if the rat does not withdraw the paw, a value of 250 grams is recorded.

Rats are tested for baseline response prior to CFA injection. Post-CFA response is tested the next morning (about 24 hours post injection of CFA). Rats are randomized based on post-CFA response with any rat showing a score of >150 grams excluded from further testing. A test compound (prodrug) is orally dosed within a range of 1.5 to 15 mg/kg and mechanical threshold for paw withdrawal is measured at 1 and 2 hours post dosing. Statistical significance is defined as a p value <0.05 in an analysis of covariance followed by a Dunnett's post hoc test for each time point. Table 2 below provides the statistically significant results for Example 10 run substantially as above. These results demonstrate that compounds within the scope of the present invention are useful medications for chronic inflammatory pain conditions such as osteoarthritis or rheumatoid arthritis.

TABLE 2

| | Paw withdrawal Threshold (grams, force) | | | |
|---|---|---|---|---|
| | Baseline (Pre CFA) | 24 hours (post CFA) | One hour (post dosing) | Two hours (post dosing) |
| Vehicle (1% HEC) | 236 ± 7 | 112 ± 9 | 98 ± 7 | 109 ± 14 |
| 1.5 mg/kg po of Example 10 | 243 ± 5 | 113 ± 8 | 180 ± 14* | 186 ± 19* |
| 4.5 mg/kg po of Example 10 | 221 ± 10 | 114 ± 9 | 153 ± 20* | 221 ± 20* |
| 15 mg/kg po of Example 10 | 244 ± 4 | 108 ± 12 | 250 ± 0* | 232 ± 15* |

Values are mean ± SEM for an N = 8-10 per group.
*p value <0.05 vs. vehicle at same time point (ANOVA and Dunnett's t-test)

Reversal of Colorectal Distension-Induced Pain Behaviors.

Visceral pain in rats can be induced by distension of the colorectal cavity and pain monitored by accessing the reflex contraction of abdominal muscles. Measurement of abdominal muscle reflex contractions with pain caused by colorectal distension in the rat is performed substantially as described by Fioramonti et al. *Neurogastroenterology and Motility* (2003) 15, 363-369 and Urban et al. *J. of Pharmacology and Exp. Ther.* (1999) 290, 207-213. Male Sprague Dawley rats are surgically implanted with electromyographic (EMG) electrodes in the oblique abdominal muscle and allowed to recover for one week, during which animals are acclimated to handling and partial restraint to minimize effects of stress. Baseline EMG measurements are collected and recorded after the insertion into the rectum (8 cm) of a lubricated latex balloon attached to a pressure monitor/regulator to step the pressure between 20, 40, and 60 mm Hg for a 20 second duration with a 3 minute resting period between trials. A set of three exposures at each pressure is recorded before stepping the pressure up to the next level. Data are collected as the area under the curve for EMG reading (volts per second) during the pressure stimulations, and averaged over the three trials. A test compound (prodrug) is orally dosed within a range of 1.5 to 17 mg/kg 90 minutes prior to the beginning of the colorectal distension. Statistical significance is defined as a p value <0.05 in an analysis of covariance followed by a Dunnett's post hoc test. Table 3 below provides the statistically significant results for Example 10 run substantially as above. These results demonstrate that compounds within the scope of the present invention are useful medications for visceral pain conditions.

TABLE 3

| AUC of EMG reading for abdominal muscle (µV/sec) | AUC of EMG reading for abdominal muscle (µV/sec) with 60 mmHg colorectal pressure | |
|---|---|---|
| with 60 mmHg colorectal pressure | Baseline (pre-dosing) | 90 minutes (post dosing) |
| Vehicle (1% HEC) | 813 ± 101 | 849 ± 65 |
| 1.5 mg/kg po of example 10 | 853 ± 142 | 618 ± 92 |
| 4.5 mg/kg po of example 10 | 887 ± 152 | 531 ± 99* |
| 17 mg/kg po of example 10 | 773 ± 134 | 266 ± 87* |

Values are mean ± SEM for an N = 8-16 per group.
*p value <0.05 vs. vehicle at same time point (ANOVA and Dunnett's t-test)

Reversal of Phencyclidine (PCP)-Induced Hyperlocomotor Activity in Rats

Administration of NMDA receptor antagonists, such as ketamine or phencyclidine (PCP), produces psychotomimetic-like effects in humans that are similar to those symptoms observed in patients with schizophrenia. The ability of agents to reverse the locomotor-stimulating effects of NMDA antagonists are often used as an animal model of psychosis, demonstrating good predictive validity for detecting clinical efficacy of medications for schizophrenia and bipolar disorder.

Motor activity is monitored by placing individual male, Sprague-Dawley (Harlan, Indianapolis, Ind.) rats in transparent, plastic shoe-box cages of the dimensions 45×25×20 cm, with 1 cm depth of wood chips as bedding, and a metal grill on top of the cage. Motor monitors (Kinder Scientific) consist of a rectangular rack of 12 photobeams arranged in an 8×4 formation, (or a high density grouping of 22 in a 15×7 pattern) at a height of 5 cm, with a second rack (for measuring rearing behaviors) at a height of 15 cm. The shoe box cage is placed inside of these racks, with the racks on a 3 foot high tabletop in an isolated room. A compound of the invention (active) is dosed (intraperitoneal route) within a range of 0.3-10 mg/kg, 30 minutes prior to a 5 mg/kg challenge dose of phencyclidine (PCP). A compound of the invention (prodrug) is orally dosed within a range of 0.3-30 mg/kg, in overnight fasted rats, 4 hours prior to a 5 mg/kg challenge dose of PCP. On the test day, rats are placed in the test cage and allowed to acclimate for 30 minutes prior to PCP challenge; rats are monitored for an additional 60 minutes following PCP administration.

Data analysis and $ED_{50}$ calculations are conducted using GraphPad Prism (San Diego, Calif. USA). Power analyses have determined that 8-10 rats per group are needed to have appropriate statistical power for detecting treatment differences (power=0.8). A one-way analysis of variance (ANOVA) with a post-hoc Dunnett's multiple comparison test is conducted on the total 60 minute locomotor activity. $ED_{50}$ calculations are performed using non-linear regression curve fitting on percent reversal transformed data for each dose.

Example 2 is measured in this assay run substantially as above to have an $ED_{50}$ of 1.46 mg/kg (i.p.). Examples 5 and 6 are measured in this assay run substantially as above to have 2.95 mg/kg (p.o.) and 4.31 mg/kg (p.o.), respectively. These results demonstrate that compounds within the scope of the present invention are useful medications for schizophrenia and bipolar disorder.

Attenuation of Stress-Induced Hyperthermia in Rats

Hyperthermia, a rise in core body temperature, is a general phenomenon that has been reliably demonstrated in many mammals, including humans, in response to stress. In many anxiety disorders, hyperthermia occurs as part of the pathology and is considered a symptom of the disease. Compounds which attenuate stress-induced hyperthermia in animals are believed to be useful in treating anxiety disorders in humans. Generalized anxiety disorder and post traumatic stress disorder are among the disorders that may be treated with such compounds. The conventional and minimally-invasive method for analyzing stress-induced hyperthermia is by measuring body temperature, and stress-induced increases in body temperature, via rectal thermometer. Male Fischer F-344 rats (Harlan, Indianapolis, Ind., USA) weighing between 275-350 g are tested. All animals are individually-housed with food and automated water available ad libitum, and maintained on a 12 h light/dark cycle (lights on at 06:00). Animals are fasted for approximately 12-18 hours before the experiment, which is conducted during the light phase. Rats are dosed intraperitoneal (IP) in a dose volume of 1 mL/kg with compounds of the invention in the range of 0.3, 1, 3, and 10, mg/kg. Vehicle is saline+NaOH added to achieve a pH of 5-7. The mGluRS antagonist MTEP (3-[(2-methyl-1,3-thiazol-4-yl)ethynyl]pyridine), which has demonstrated robust anxiolytic-like activity in preclinical models, is used as a comparator (5 mg/kg, IP route, dissolved in water). Immediately following dosing, rats are returned to their home cage, and the experimenter turns off the lights and leaves the room. The dosing room is darkened for the remainder of the 1-hr pretreatment period.

After the pretreatment period, rats are taken individually to a brightly lit adjacent room where baseline body temperatures are determined by insertion of a rectal probe lubricated with mineral oil. Body temperature is assessed using a PHYSITEMP BAT-12® Microprobe Thermometer with a PHYSITEMP RET-2® rat rectal probe (Physitemp Instruments Inc., Clifton, N.J., USA). The probe is inserted approximately 2 cm into the rectum, to measure the core body temperature (this is the baseline body temperature, T1, in degrees Celsius). Ten minutes later a second body temperature measurement is recorded (T2). The difference in body temperature (T2−T1) is defined as the stress-induced hyperthermic response. The dose at which a compound of the invention produces a 35% reduction in stress-induced hyperthermic response, relative to the vehicle response, is defined as the $T_{35}$ dose.

Example 2 is measured in this assay run substantially as above to have a $T_{35}$ of 0.57 mg/kg. Example 5 is measured in this assay run substantially as above to have a $T_{35}$ of 6.4 mg/kg. These results demonstrate that compounds within the scope of the present invention are useful medications for anxiety disorders. More particularly, compounds within the scope of the present invention may be useful medications for generalized anxiety disorder and/or post traumatic stress disorder.

In Vitro PepT1 GlySar Inhibition Screen and $IC_{50}$ Determination

PepT1 assays are established to examine the ability of the prodrugs to interact with the intestinal absorption transporter PepT1.

HeLa cells, derived from human intestine, (American Type Culture Collection) are grown in Hyclone Medium (Invitrogen, Cat# SH30243) containing 10% fetal bovine serum (FBS), 0.1 mM non essential amino acids (NEAA), and 100 units/mL penicillin with 100 µg/mL streptomycin at 37° C. in a 5% $CO_2$ humidified atmosphere. The cell line is used for up to 40 passages and then discarded. Frozen cells in 1 ml vials are thawed in water bath for 1-2 minutes and added to 5 mL of cell medium at 37° C. Each of the T-flasks is provided with 8.5 mL of the fresh medium and 1.5 mL of the cell stock. Cells are passaged twice during a week. This is achieved by rinsing the flasks with 10 mL of phosphate buffered saline-ethylene diaminetetra acetic acid (PBS-EDTA), adding 2 mL of trypsin for 2-5 minutes, to detach the cells, and adding 8 mL of fresh medium to inhibit further activity of trypsin. Each new flask receives a combination of 8.5 mL of fresh medium and 1.5 mL of cell stock, in order to obtain 1:6 cell dilution. Cells are incubated at 37° C., until ready for the uptake study.

Cells that are 70-80% confluent in the T-flasks are plated 1 day prior to the transfection procedure. The flask with the cell stock is treated with PBS-EDTA and trypsin to detach the cells, and transfection medium is used from this point. Transfection medium consists of Dulbecco's Modified Eagle Medium (DMEM)+NEAA. To each well, 0.5 mL of the cell mixture is added ($1.3 \times 10^5$ is the desired cell concentration) and the cells are incubated at 37° C. overnight. Twenty four hours before the assay, cells are transfected with PEPT1. Transfection mixture is prepared by mixing 600 µL of serum free transfection medium, 18 µL of FuGene6 (Roche Diagnostics), and 11 µg of the PepT1 DNA. The transfection reagent-DNA complex is incubated for 20 minutes and 24 µL of the reagent-DNA complex is added to each well.

Inhibition of PEPT1-mediated [glycyl-1-2-$^{14}$C]Glyclysarcosine (GlySar) uptake activity is measured in the cells cultured in the 24-well plates 24-hours post transfection as previously published (Zhang et al. 2004. J. Pharm. Exper Ther. 310:437-445). To measure the ability of a compound of the invention to inhibit the uptake of [$^{14}$C]Gly-Sar, prodrugs are incubated with 80 to 90% confluent PepT1 transiently transfected HeLa cells at 5 mM in pH 6.0 uptake medium in the presence of 5 µM [$^{14}$C]Gly-Sar (Moravek Biochemicals) and 20 µM cold Gly-Sar. Uptake media consists of 140 mM NaCl, 5.4 mM KCl, 1.8 mM $CaCl_2$, 0.8 mM $MgSO_4$, 5 mM Glucose, 25 mM tris(hydroxymethyl)aminomethane buffer (TRIS). The solution is then brought to pH 6.0 using 2-(N-morpholino)ethanesulfonic acid. The incubation volume is 500 µL and is performed at room temperature for 3 minutes. To stop the uptake at the conclusion of the incubation time, the uptake media is aspirated off of the cell monolayer and 500 µL of ice cold PBS added to the well. The cells are washed 3 times with 500 µL of room temperature PBS without $Ca^{+2}$ and $Mg^{+2}$. The cells are then lysed with 300 µL of 1% Triton X100 $H_2O$ solution. A 200 µL aliquot is removed and radioactivity is determined by liquid scintillation counting to measure the [$^{14}$C]Gly-Sar present in each of the incubation wells. A no inhibitor control is established and the percent inhibition of each prodrug is calculated with respect to this control. A negative control (Glycine) and two positive controls (Cefadroxil and Cefalexin) are performed in parallel with each experiment to demonstrate viability of the assay system. Prodrugs with GlySar uptake inhibition equal or better than Cephalexin are considered acceptable. Mean values±standard deviation are 10.1±9.5% (n=19) for Glycine, 53.2±13.2% (n=19) for Cefadroxil, and 37.5±14.7% (n=18) for Cephalexin.

For the PepT $IC_{50}$ assay, prodrugs are incubated at a range of concentrations (0.0625 to 25 mM) in the presence of 5 µM [$^{14}$C]Gly-Sar and 20 µM cold Gly-Sar. The incubation and sampling procedures are exactly the same as the PepT1 screen described above. [$^{14}$C]Gly-Sar uptake data are evaluated for each of the prodrug concentrations and IC$_{50}$ values are calculated.

Examples 5, 6, and 7 are measured in this assay run substantially as above to have hPepT1 [3H]Gly-Sar uptake inhibition at 5 mM of 89%, 87%, and 78%, respectively. Examples 5 and 6 are measured in this assay run substantially as above to have hPepT1 [3H]Gly-Sar uptake inhibition IC50 of 1.98 mM and 0.25 mM, respectively. These results demonstrate that compounds within the scope of the present invention are orally absorbed via the PepT1 transporter.

In Vitro Intestinal Prodrug Hydrolysis Assay

Frozen human duodenum intestinal homogenates (1:2 tissue:buffer ratio using 100 mM Tris Phosphate buffer, pH 7.4) are obtained from Celsius In Vitro Technologies (Baltimore, Md.) that were both phenylmethylsulphonylfluoride (PMSF) and EDTA free.

Each lot of human duodenum is obtained from a single donor and the intestine is scraped and the sections are frozen separate. All original tissue collections are performed at 4° C. and immediately frozen at −70° C. Human intestinal homogenates are thawed and diluted to a final protein concentration of 0.5 mg/mL in 100 mM PBS buffer, pH 7.4 immediately prior to the incubations.

Incubations are conducted in 96-well plates and all prodrugs are run in duplicate on each day. Stock prodrug solutions are prepared in water at a concentration of 1 mM. A 200 µL aliquot of 0.5 mg/mL intestinal homogenate and 196 µL of 100 mM PBS buffer are placed in a 96-well plate in a 37° C. water bath. Using a 96-well pipettor, 4 µL of the 1 mM prodrug solution is transferred into the homogenate. Immediately after addition of the prodrug (time zero) and after 1 hour incubation, 50 µL samples of the incubation mixture are removed using an automated disposable simultaneous 96 well pipettor and added directly to 200 µL of methanol quench solution containing 100 ng/mL of Internal Standard. The samples are then centrifuged at 3500 rpm for 5 minutes at 10° C. The supernatant (200 µL) is transferred to a final 96 well PCR plate and sealed for analysis by LC/MS/MS.

Concentrations of hydrolyzed active metabolite in the incubation mixtures are determined using LC/MS/MS detection on a Sciex API 4000 quadrapole mass spectrometer with Analyst version 1.4.2, TurbolonSpray, positive ionization, and Selected Reaction Monitoring (SRM). A Waters Atlantis® T3 (20×2.1 mm, 5 µM) HPLC column is used at ambient temperature with a flow rate of 1.0 mL/min and a mobile phase gradient from 0.1% mobile phase A to 99% mobile phase A. Mobile phase A is 1000:5 water:heptafluorobuteric acid and mobile phase B is 1:1 methanol:glacial acetic acid.

Concentrations of hydrolyzed active metabolite in the intestinal incubation mixtures are determined from standard curves prepared by replicate two-fold dilution starting at 10 µM in 100 mM PBS pH 7.4 and subsequently quenched with methanol-internal standard solution identical to the samples. Averages and standard deviations are calculated using Microsoft® Office Excel® 2007. Amount of hydrolysis is determined as a molar percentage of active metabolite formed relative to prodrug concentration added. Hydrolysis of the positive control, Internal Prodrug A to Internal Active Metabolite Drug A, run in every batch averaged 75.3% (n=20). Final values are then normalized relative to the formation of Internal Active Metabolite Drug A.

Examples 5, 6, and 7 are measured in this assay run substantially as above to have human intestinal hydrolysis relative to Internal Prodrug A of 36% (n=3, SD=2.7), 44% (n=3, SD=4.1), and 34% (n=1), respectively. These results demonstrate that compounds within the scope of the present invention are hydrolyzed in the human intestine.

In Vitro Human Liver S-9 Homogenate Hydrolysis Assay

Liver S9 fractions are obtained from Xenotech LLC (Lenexa, Mo.). The lot is from a pool of two donors, one male and one female. The liver S9 fraction is prepared and diluted using a homogenization buffer consisting of 50 mM Tris, pH 7.4 at 4° C. and 150 mM potassium chloride without EDTA. Prodrugs are incubated in the liver homogenate for 2 hours at 37° C., after which the concentration of active metabolite is determined by LC/MS/MS. Hydrolysis of Clopidogrel to Clopidogrel Carboxylic Acid is utilized as an assay positive control.

Incubations are conducted in 96-well format and all prodrugs are run in duplicate on each day. Stock prodrug solutions are prepared in water at a concentration of 1 mM. Human liver S9 fraction is diluted to a final protein concentration of 0.5 mg/ml in 100 mM PBS buffer, pH 7.4.

A 200 µL aliquot of 0.5 mg/mL human liver S-9 homogenate and 196 µL of 100 mM PBS buffer are placed in a 96-well plate in a 37° C. water bath. Using a 96-well pipettor, 4 µL of the 1 mM prodrug solution is transferred into the homogenate. To ensure hydrolysis is not due to chemical instability, prodrugs are also incubated with PBS buffer alone without liver S-9. Immediately after addition of the prodrug (time zero) and after 1 hour incubation, 50 µL samples of the incubation mixture are removed using an automated disposable simultaneous 96-well pipettor and added directly to 200 µL of methanol quench solution containing 100 ng/mL of Internal Standard. The samples are then centrifuged at 3500 rpm for 5 minutes at 10° C. The supernatant (200 uL) is transferred to a final 96 well PCR plate and sealed for analysis by LC/MS/MS.

LC/MS/MS quantification of active metabolite formed during the incubation is performed on a Sciex API 4000, Analyst version 1.4.2, TurbolonSpray, positive ionization, and Selected Reaction Monitoring (SRM). The HPLC column used is a Waters Atlantis® T3 (20×2.1 mm, 5 µm) at ambient temperature with a mobile phase flow rate of 1.0 mL/min Mobile phase A is 1000:5 water:heptafluorobuteric acid and mobile phase B is 1:1 methanol/glacial acetic acid. A mobile phase gradient is utilized starting mobile phase ratio A/B of 99.9/0.1 and finishing at 1/99.

Concentrations of hydrolyzed active metabolite in the incubation mixtures are determined from standard curves prepared by replicate two-fold dilution starting at 10 µM in 100 mM PBS pH 7.4 and subsequently quenched with methanol-internal standard solution identical to the samples. Averages and standard deviations are calculated using Microsoft® Office Excel® 2007. Final values are presented as a molar percentage of active metabolite formed relative to prodrug concentration added. Hydrolysis of Clopidogrel to Clopidogrel Carboxylic Acid is used as the positive control and averages 73.0% (n=27).

Examples 8 and 9 are measured in this assay run substantially as above to have human liver S9 hydrolysis of 23% and 59.3%, respectively. These results demonstrate that compounds within the scope of the present invention are hydrolyzed in the human liver.

The data demonstrate that the exemplified amino acid prodrugs inhibit the uptake of the PepT1 substrate GlySar as good as or better than cefadroxil and cephalexin (Zhang et al, 2004. JPET 310:437-445), suggesting potential for human oral absorption via the PepT1 transporter. In addition to prodrug absorption, upon entering the body, prodrug hydrolysis to yield the active metabolite is essential. The present in vitro hydrolysis studies suggest the exemplified amino acid prodrugs can be hydrolyzed by human intestine. Hydrolysis of the exemplified diester prodrugs occur in human liver homogenates suggesting the potential for the exemplified diester prodrugs to have hydrolysis in humans following oral exposure. Together these data indicate the potential for the exemplified amino acid prodrugs and exemplified diester prodrugs to be hydrolyzed in humans to liberate the active metabolite.

Pharmacokinetics Assay

Fasted, male Sprague Dawley rats are administered Example 2 intravenously at 1 mg/kg or Example 5 by oral gavage at a dose of 7.5 mg/kg (equal to a 5 mg/kg molar equivalents of Example 2) in a standard cross-over design (N=3 with each rat receiving both an intravenous and oral dose). For intravenous administration, Example 2 is dissolved in water and for the oral dose Example 5 is prepared in an aqueous vehicle of hydroxyethylcellulose (1%), polysorbate 80 (0.25%) and antifoam 1510-US (0.05%). Cannulas are surgically implanted to facilitate serial blood collection. Blood is collected in EDTA tubes over a period of 0-24 hours post-dosing, centrifuged and plasma is stored frozen until time of analysis.

Plasma samples are thawed, 50 μL aliquots are transferred to a 96-well plate, 50 μL of internal standard solution is added, and the samples are mixed. Three hundred μL of acetonitrile is then added, the samples are vortexed for 3 minutes and centrifuged. A 300 μL aliquot of the supernatant is transferred to a separate plate and evaporated under nitrogen at 40 degrees C. The residue is reconstituted in 100 μL of 0.5% heptafluorobutyric acid in water, vortexed, and centrifuged. A 20 μL aliquot is subsequently analyzed by LC/MS/MS using a Shimadzu autosampler and HPLC system interfaced with an AB Sciex 4000 mass spectrometer under positive ion turbospray mode. MS/MS transitions are 283.2->44.2 amu for prodrug Example 5 and 212.1->103.1 amu for active Example 2. An Atlantis T3, 50×2.1 mm, 5 micron HPLC column at a mobile phase flow rate of 1.0 mL/minute and a binary mobile phase of (A) 0.2% formic acid in water and (B) acetonitrile-water (1:1, v/v) and a gradient of 2% B to 98% B over 0.8 minutes is utilized. The retention time of Example 2 is approximately 0.53 minutes.

Pharmacokinetic parameters are calculated from the plasma concentration data using Watson for Windows (Thermo Scientific). Relative oral bioavailability is determined by comparing the area under the plasma concentration time curve (AUC) of active Example 2 after intravenous administration with the AUC of active metabolite after oral administration of the prodrug Example 5.

A successful prodrug must be both well absorbed after oral administration and subsequently hydrolyzed to release the active metabolite into the systemic circulation. Relative bioavailability includes both parameters by comparing the AUC of active metabolite after oral administration of prodrug to the AUC of active after intravenous administration of the active compound. In male rats, the relative bioavailability of active metabolite after oral administration of prodrug Example 5 as measured in this assay run substantially as above is 60±14% (mean±standard deviation) demonstrating the prodrug Example 5 is both well absorbed and extensively hydrolyzed to yield the active metabolite in vivo.

We claim:
1. A compound of Formula I

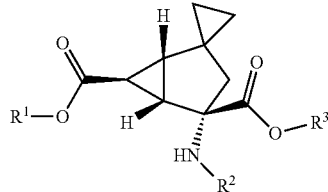

Formula I wherein
$R^1$ is hydrogen, $R^2$ is hydrogen, and $R^3$ is hydrogen;
$R^1$ is hydrogen, $R^2$ is (2S)-2-aminopropanoyl, and $R^3$ is hydrogen;
$R^1$ is hydrogen, $R^2$ is (2S)-2-amino-4-methylsulfanyl-butanoyl, and $R^3$ is hydrogen;
$R^1$ is hydrogen, $R^2$ is 2-aminoacetyl, and $R^3$ is hydrogen;
$R^1$ is benzyl, $R^2$ is hydrogen, and $R^3$ is benzyl; or
$R^1$ is (2-fluorophenyl)methyl, $R^2$ is hydrogen, and $R^3$ is (2-fluorophenyl)methyl;
or a pharmaceutically acceptable salt thereof.

2. The compound according to claim 1 which is (1S,2S,5R,6S)-2-aminospiro[bicyclo[3.1.0]hexane-4,1'-cyclopropane]-2,6-dicarboxylic acid, or a pharmaceutically acceptable salt thereof.

3. The compound according to claim 1 which is (1S,2S,5R,6S)-2-aminospiro[bicyclo[3.1.0]hexane-4,1'-cyclopropane]-2,6-dicarboxylic acid hydrochloride.

4. The compound according to claim 1 which is (1S,2S,5R,6S)-2-[[(2S)-2-aminopropanoyl]amino]spiro[bicyclo[3.1.0]hexane-4,1'-cyclopropane]-2,6-dicarboxylic acid, or a pharmaceutically acceptable salt thereof.

5. The compound according to claim 1 which is (1S,2S,5R,6S)-2-[[(2S)-2-aminopropanoyl]amino]spiro[bicyclo[3.1.0]hexane-4,1'-cyclopropane]-2,6-dicarboxylic acid hydrochloride.

6. The compound according to claim 1 which is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

7. The compound according to claim 1 which is (1S,2S,5R,6S)-2-[[(2S)-2-aminopropanoyl]amino]spiro[bicyclo[3.1.0]hexane-4,1'-cyclopropane]-2,6-dicarboxylic acid; 1,4-dioxane (1:0.5); hydrochloride.

8. The compound according to claim 1 which is (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid, or a pharmaceutically acceptable salt thereof.

9. The compound according to claim 1 which is (1S,2S,5R,6S)-2-[[(2S)-2-amino-4-methylsulfanyl-butanoyl]amino]spiro[bicyclo[3.1.0]hexane-4,1'-cyclopropane]-2,6-dicarboxylic acid hydrochloride.

10. The compound according to claim 1 which is (1S,2S,5R,6S)-2-[(2-aminoacetyl)amino]spiro[bicyclo[3.1.0]hexane-4,1'-cyclopropane]-2,6-dicarboxylic acid, or a pharmaceutically acceptable salt thereof.

11. The compound according to claim 1 which is (1S,2S,5R,6S)-2-[(2-aminoacetyl)amino]spiro[bicyclo[3.1.0]hexane-4,1'-cyclopropane]-2,6-dicarboxylic acid hydrochloride.

12. The compound according to claim 1 which is dibenzyl (1S,2S,5R,6S)-2-aminospiro[bicyclo[3.1.0]hexane-4,1'-cyclopropane]-2,6-dicarboxylate, or a pharmaceutically acceptable salt thereof.

13. The compound according to claim 1 which is dibenzyl (1S,2S,5R,6S)-2-aminospiro[bicyclo[3.1.0]hexane-4,1'-cyclopropane]-2,6-dicarboxylate; 1,4-dioxane; hydrochloride.

14. The compound according to claim 1 which is bis[(2-fluorophenyl)methyl](1S,2S,5R,6S)-2-aminospiro[bicyclo[3.1.0]hexane-4,1'-cyclopropane]-2,6-dicarboxylate, or a pharmaceutically acceptable salt thereof.

15. The compound according to claim 1 which is bis[(2-fluorophenyl)methyl](1S,2S,5R,6S)-2-aminospiro[bicyclo[3.1.0]hexane-4,1'-cyclopropane]-2,6-dicarboxylate hydrochloride.

16. A pharmaceutical composition comprising a compound of Formula I

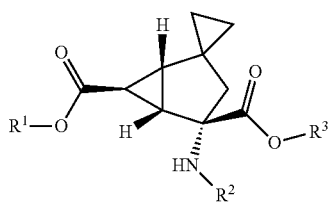

Formula I wherein $R^1$ is hydrogen, $R^2$ is hydrogen, and $R^3$ is hydrogen;

$R^1$ is hydrogen, $R^2$ is (2S)-2-aminopropanoyl, and $R^3$ is hydrogen;

$R^1$ is hydrogen, $R^2$ is (2S)-2-amino-4-methylsulfanyl-butanoyl, and $R^3$ is hydrogen;

$R^1$ is hydrogen, $R^2$ is 2-aminoacetyl, and $R^3$ is hydrogen;

$R^1$ is benzyl, $R^2$ is hydrogen, and $R^3$ is benzyl; or $R^1$ is (2-fluorophenyl)methyl, $R^2$ is hydrogen, and $R^3$ is (2-fluorophenyl)methyl;

or a pharmaceutically acceptable salt thereof, and a pharmaceutically acceptable carrier, diluent, or excipient.

17. The pharmaceutical composition according to claim 16 wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

18. A method of treating a neurological disorder selected from the group consisting of persistent pain, neuropathic pain, chronic inflammatory pain, and visceral pain, comprising administering to a patient in need thereof an effective amount of a compound of Formula I

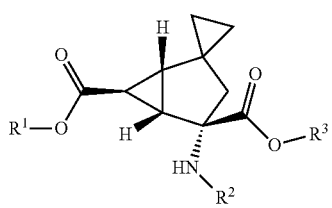

Formula I wherein $R^1$ is hydrogen, $R^2$ is hydrogen, and $R^3$ is hydrogen;

$R^1$ is hydrogen, $R^2$ is (2S)-2-aminopropanoyl, and $R^3$ is hydrogen;

$R^1$ is hydrogen, $R^2$ is (2S)-2-amino-4-methylsulfanyl-butanoyl, and $R^3$ is hydrogen;

$R^1$ is hydrogen, $R^2$ is 2-aminoacetyl, and $R^3$ is hydrogen;

$R^1$ is benzyl, $R^2$ is hydrogen, and $R^3$ is benzyl; or $R^1$ is (2-fluorophenyl)methyl, $R^2$ is hydrogen, and $R^3$ is (2-fluorophenyl)methyl;

or a pharmaceutically acceptable salt thereof.

19. The method of claim 18, wherein the neurological disorder is persistent pain.

20. The method of claim 18, wherein the neurological disorder is neuropathic pain.

21. The method of claim 18 wherein the neurological disorder is chronic inflammatory pain.

22. The method of claim 18, wherein the neurological disorder is visceral pain.

23. The method of claim 19, wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

24. The method of claim 20, wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

25. The method of claim 21 wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

26. The method of claim 22, wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

27. A method of treating a psychiatric disorder selected from the group consisting of schizophrenia, bipolar disorder, generalized anxiety disorder, and post traumatic stress disorder, comprising administering to a patient in need thereof an effective amount of a compound of Formula I

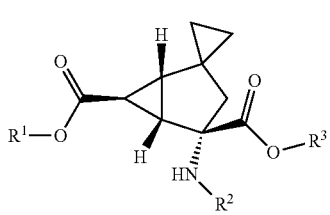

Formula I wherein $R^1$ is hydrogen, $R^2$ is hydrogen, and $R^3$ is hydrogen;

$R^1$ is hydrogen, $R^2$ is (2S)-2-aminopropanoyl, and $R^3$ is hydrogen;

$R^1$ is hydrogen, $R^2$ is (2S)-2-amino-4-methylsulfanyl-butanoyl, and $R^3$ is hydrogen;

$R^1$ is hydrogen, $R^2$ is 2-aminoacetyl, and $R^3$ is hydrogen;

$R^1$ is benzyl, $R^2$ is hydrogen, and $R^3$ is benzyl; or $R^1$ is (2-fluorophenyl)methyl, $R^2$ is hydrogen, and $R^3$ is (2-fluorophenyl)methyl;

or a pharmaceutically acceptable salt thereof.

28. The method of claim 27, wherein the psychiatric disorder is schizophrenia.

29. The method of claim 27, wherein the psychiatric disorder is bipolar disorder.

30. The method of claim 27 wherein the psychiatric disorder is generalized anxiety disorder.

31. The method of claim 27, wherein the psychiatric disorder is post traumatic stress disorder.

32. The method of claim 28, wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

33. The method of claim 29, wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

34. The method of claim 30 wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

35. The method of claim 31, wherein the compound is (1S,2S,5R,6S)-2-[[(2S)-2-aminopropanoyl]amino]spiro[bicyclo[3.1.0]hexane-4,1'-cyclopropane]-2,6-dicarboxylic acid dihydrate.

* * * * *